United States Patent
Jia et al.

(10) Patent No.: US 11,826,191 B2
(45) Date of Patent: *Nov. 28, 2023

(54) SYSTEM AND METHOD FOR MEDICAL IMAGING OF INTERVERTEBRAL DISCS

(71) Applicant: SHANGHAI UNITED IMAGING HEALTHCARE CO., LTD., Shanghai (CN)

(72) Inventors: Fenggang Jia, Shanghai (CN); Wenjun Yu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/449,085

(22) Filed: Sep. 27, 2021

(65) Prior Publication Data

US 2022/0008028 A1    Jan. 13, 2022

Related U.S. Application Data

(63) Continuation of application No. 16/225,777, filed on Dec. 19, 2018, now Pat. No. 11,129,582.

(30) Foreign Application Priority Data

Dec. 21, 2017  (CN) .......................... 201711396812.2

(51) Int. Cl.
*G06T 7/00* (2017.01)
*A61B 6/00* (2006.01)
(Continued)

(52) U.S. Cl.
CPC .............. *A61B 6/5223* (2013.01); *A61B 6/03* (2013.01); *A61B 6/032* (2013.01); *A61B 6/505* (2013.01);
(Continued)

(58) Field of Classification Search
CPC ......... A61B 6/5223; A61B 6/03; A61B 6/032; A61B 6/505; A61B 6/5252; A61B 6/5258;
(Continued)

(56) References Cited

U.S. PATENT DOCUMENTS 7,548,638 B2    6/2009  Graessner
8,423,124 B2 *  4/2013  Kiraly ..................... G06T 7/155
                                                600/443
(Continued)

FOREIGN PATENT DOCUMENTS

CN       106157288 A       11/2016
CN       106485704 A        3/2017
(Continued)

OTHER PUBLICATIONS

Darko Štern* et al., Automated Detection of Spinal Centrelines, Vertebral Bodies and Intervertebral Discs in CT and MR Images of Lumbar Spine, Physics in Medicine and Biology, 2010, 17 pages.
(Continued)

*Primary Examiner* — Shefali D Goradia
(74) *Attorney, Agent, or Firm* — METIS IP LLC

(57) ABSTRACT

The present disclosure directs to a system and method for image processing. The method for image processing comprises acquiring a plurality of original computed tomography (CT) images of a spine of a subject; generating CT value images of the spine of the subject by processing the plurality of original CT images. The method further includes identifying an optimal sagittal image in which a centerline of the spine is located based on the CT value images. The method further includes identifying the centerline of the spine within the optimal sagittal image. The method further includes identifying a center point and a direction of at least one intervertebral disc along the centerline of the spine. The
(Continued)

method still further includes reconstructing an image of the at least one intervertebral disc based on the center point and the direction of the at least one intervertebral disc.

18 Claims, 17 Drawing Sheets

(51) Int. Cl.
 *G16H 30/40* (2018.01)
 *A61B 6/03* (2006.01)
 *G06T 11/00* (2006.01)

(52) U.S. Cl.
 CPC .......... *A61B 6/5252* (2013.01); *A61B 6/5258* (2013.01); *G06T 7/0012* (2013.01); *G06T 11/003* (2013.01); *G16H 30/40* (2018.01); *G06T 2207/10081* (2013.01); *G06T 2207/30012* (2013.01)

(58) Field of Classification Search
 CPC ..... G16H 30/40; G06T 7/0012; G06T 11/003; G06T 2207/10081; G06T 2207/30012
 See application file for complete search history.

(56) References Cited

U.S. PATENT DOCUMENTS

| | | | |
|---|---|---|---|
| 10,140,543 B2* | 11/2018 | Dong | G06T 7/11 |
| 10,872,415 B2* | 12/2020 | Cheng | G06T 7/143 |
| 10,874,460 B2 | 12/2020 | Schmidt et al. | |
| 2005/0197562 A1 | 9/2005 | Graessner | |
| 2006/0110017 A1 | 5/2006 | Tsai et al. | |
| 2008/0137932 A1 | 6/2008 | Shen et al. | |
| 2008/0273775 A1 | 11/2008 | Hilbelink | |
| 2013/0322727 A1 | 12/2013 | Goto | |
| 2016/0089074 A1 | 3/2016 | Wang | |
| 2021/0150724 A1* | 5/2021 | Cheng | G06T 7/11 |

FOREIGN PATENT DOCUMENTS

| | | |
|---|---|---|
| CN | 106600609 A | 4/2017 |
| CN | 106709925 A | 5/2017 |
| CN | 106960439 A | 7/2017 |

OTHER PUBLICATIONS

Cheng, Shiyin et al., Centerline Extraction from MR Carotid Angiography Images, Chinese Journal of Stereology and Image Analysis, 21(4): 415-422, 2016.

First Office Action in Chinese Application No. 201711396812.2 dated Nov. 6, 2020, 15 pages.

* cited by examiner

SYSTEM AND METHOD FOR MEDICAL IMAGING OF INTERVERTEBRAL DISCS

CROSS-REFERENCE TO RELATED APPLICATIONS

This application is a continuation of U.S. patent application Ser. No. 16/225,777, filed on Dec. 19, 2018, which claims priority of Chinese Patent Application No. 201711396812.2, filed on Dec. 21, 2017, the contents of which are hereby incorporated by reference.

TECHNICAL FIELD

The present disclosure generally relates to medical imaging, and more particularly to a system and method for imaging of intervertebral discs of a spine of a subject.

BACKGROUND

Computed tomography (CT) is a technology that makes use of computer-processed combinations of X-ray images taken from different angles to produce cross-sectional images. The CT technology has been widely used in medical diagnosis, for example, intervertebral disc imaging. However, CT images, such as CT tomographic image may not satisfy clinical requirements for diagnosis of the intervertebral disc issues since patient bodies vary in multiple aspects, for example, spinal curvature, sizes of intervertebral discs, directions of intervertebral discs, etc. Thus, there is a need for a system and method for intervertebral disc imaging.

SUMMARY

According to an aspect of the present disclosure, an image processing method is provided. The image processing method is implemented on at least one machine each of which has at least one processor and at least one storage device. The method comprises acquiring a plurality of original computed tomography (CT) images of a spine of a subject; generating CT value images of the spine of the subject by processing the plurality of original CT images; identifying an optimal sagittal image in which a centerline of the spine is located based on the CT value images; identifying the centerline of the spine within the optimal sagittal image; identifying a center point and a direction of at least one intervertebral disc along the centerline of the spine; and reconstructing an image of the at least one intervertebral disc based on the center point and the direction of the at least one intervertebral disc.

In some embodiments, generating the CT value images of the spine of the subject includes processing the plurality of original CT images of the spine by removing artifacts from the original CT images, the artifacts including a signal from a bed on which the subject is placed during the acquisition of the original CT images; and converting a gray scale value of each pixel of the original CT images into a CT value of the each pixel.

In some embodiments, identifying the optimal sagittal image in which a centerline of the spine is located comprises obtaining a first value; determining first binary images of the spine by applying the first value to the plurality of CT value images, the binary images of the spine being a plurality of two-dimensional (2D) coronal slices; forming a 2D summed image by summing the plurality of 2D coronal slices in the binary images; determining an extreme pixel in the 2D summed coronal image; and determining the optimal sagittal image based on the extreme pixel in the 2D summed image.

In some embodiments, identifying the centerline of the spine within the optimal sagittal image includes selecting a set of sagittal images located within a specified distance from the optimal sagittal image; generating a 2D minimum density projection image by applying a minimum density projection algorithm to the set of selected sagittal images; obtaining a second value; generating a second binary image by applying the second value to the 2D minimum density projection image; generating a dilated map by applying a morphological dilation operation to the second binary image that connect bones in the second binary image into a connected region; determining a maximum connected region in the dilated map; identifying center points of the spine; and connecting the center points sequentially to form the spine centerline.

In some embodiments, identifying a position and an orientation of the at least one intervertebral disc along the centerline of the spine includes determining a point-direction-mean value set of the spine centerline, the point-direction-mean value set including a mean value and a direction vector associated with each point on the spine centerline; and determining the position and the orientation of the at least one intervertebral disc using the point-direction-mean value set.

In some embodiments, determining the point-direction-mean set of the spine centerline comprises for each point on the centerline, identifying a normal vector perpendicular to the centerline at the point; identifying a set of direction vectors having directions within a specified range and at a specified incremental difference, the specified range encompassing the normal vector; for each direction vector in the set of direction vectors, selecting a set of pixels along the each direction vector and within the boundary of the spine; and determining a mean value associated with the each direction vector as the mean value of the direction; determining a minimum mean value among the mean values associated with the set of direction vectors; designating the minimum mean value as the mean value associated with the each point on the centerline; identifying a direction along which the minimum mean values associated with the each point on the centerline is identified; and designating the identified direction as the direction associated with the each point on the centerline.

In some embodiments, determining the center point and the direction of the at least one intervertebral disc comprises generating a point-mean value curve; smoothing the curve with a predetermined smoothing radius; shifting the curve down by a value; identifying the center point of the at least one intervertebral disc based on nadirs of the smoothed curve; and determining the direction of the at least one intervertebral disc based on the point-direction-mean value set.

In some embodiments, reconstructing the image of the at least one intervertebral disc based on the center point and the direction of the at least one intervertebral disc includes reconstructing the image of the at least one intervertebral disc according to a multiple planar reconstruction algorithm.

According to another aspect of the present disclosure, an image processing system is provided. The image processing system comprises at least one storage device storing a set of instructions; and at least one processor configured to communicate with the at least one storage device, wherein when executing the set of instructions, the at least one processor is directed to perform operations including acquiring a plurality of original computed tomography (CT) images of a spine of a subject; generating CT value images of the spine of the subject by processing the plurality of original CT images; identifying an optimal sagittal image in which a centerline of the spine is located based on the CT value images; identifying the centerline of the spine within the optimal sagittal image; identifying a center point and a direction of at least one intervertebral disc along the centerline of the spine; and reconstructing an image of the at least one intervertebral disc based on the center point and the direction of the at least one intervertebral disc.

According to a further aspect of the present disclosure, a non-transitory computer readable medium is provided. The non-transitory computer readable medium comprises at least one set of instructions, wherein when executed by at least one processor of a computing device, the at least one set of instructions causes the computing device to perform a method. The method comprises acquiring a plurality of original computed tomography (CT) images of a spine of a subject; generating CT value images of the spine of the subject by processing the plurality of original CT images; identifying an optimal sagittal image in which a centerline of the spine is located based on the CT value images; identifying the centerline of the spine within the optimal sagittal image; identifying a center point and a direction of at least one intervertebral disc along the centerline of the spine; and reconstructing an image of the at least one intervertebral disc based on the center point and the direction of the at least one intervertebral disc.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
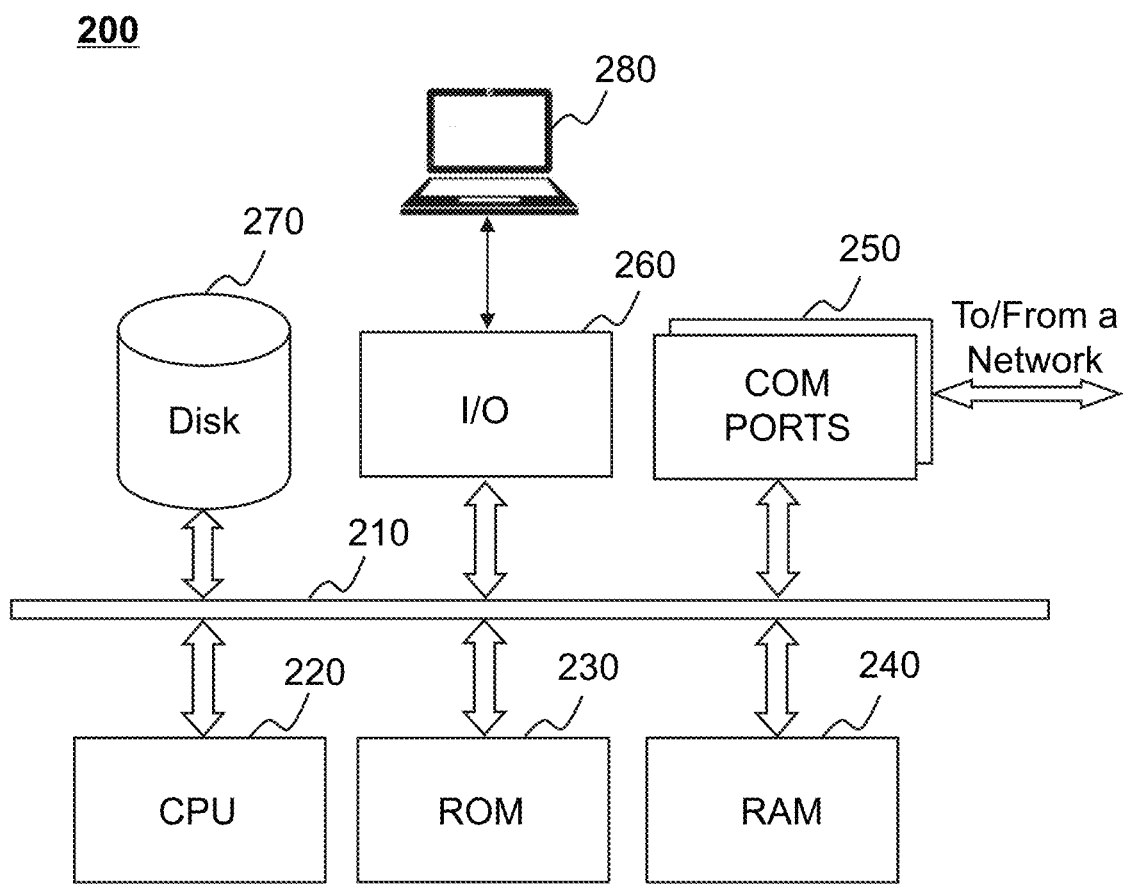
FIG. 2 is a schematic diagram illustrating exemplary components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, a magnetic resonance imaging (MRI) system, a computed tomography-positron emission tomography (CT-PET) system, an emission computed tomography (ECT) system, a computed tomography-magnetic resonance imaging (CT-MRI) system, an ultrasonography system, an X-ray photography system, or the like, or any combination thereof.

For illustration purposes, the disclosure is directed to systems and methods for CT imaging of intervertebral discs in a spine of a subject. To reconstruct an image of an intervertebral disc, the plane on which the intervertebral disc is may be determined. The system may determine a center point and a direction of the intervertebral disc so as to determine the plane on which the intervertebral disc is. A series of operations including image conversion, image segmentation, morphological dilation operation, morphological closing operation, reconstruction operation, etc., may be performed to determine the center point and the direction of the intervertebral disc.

Figure 1:
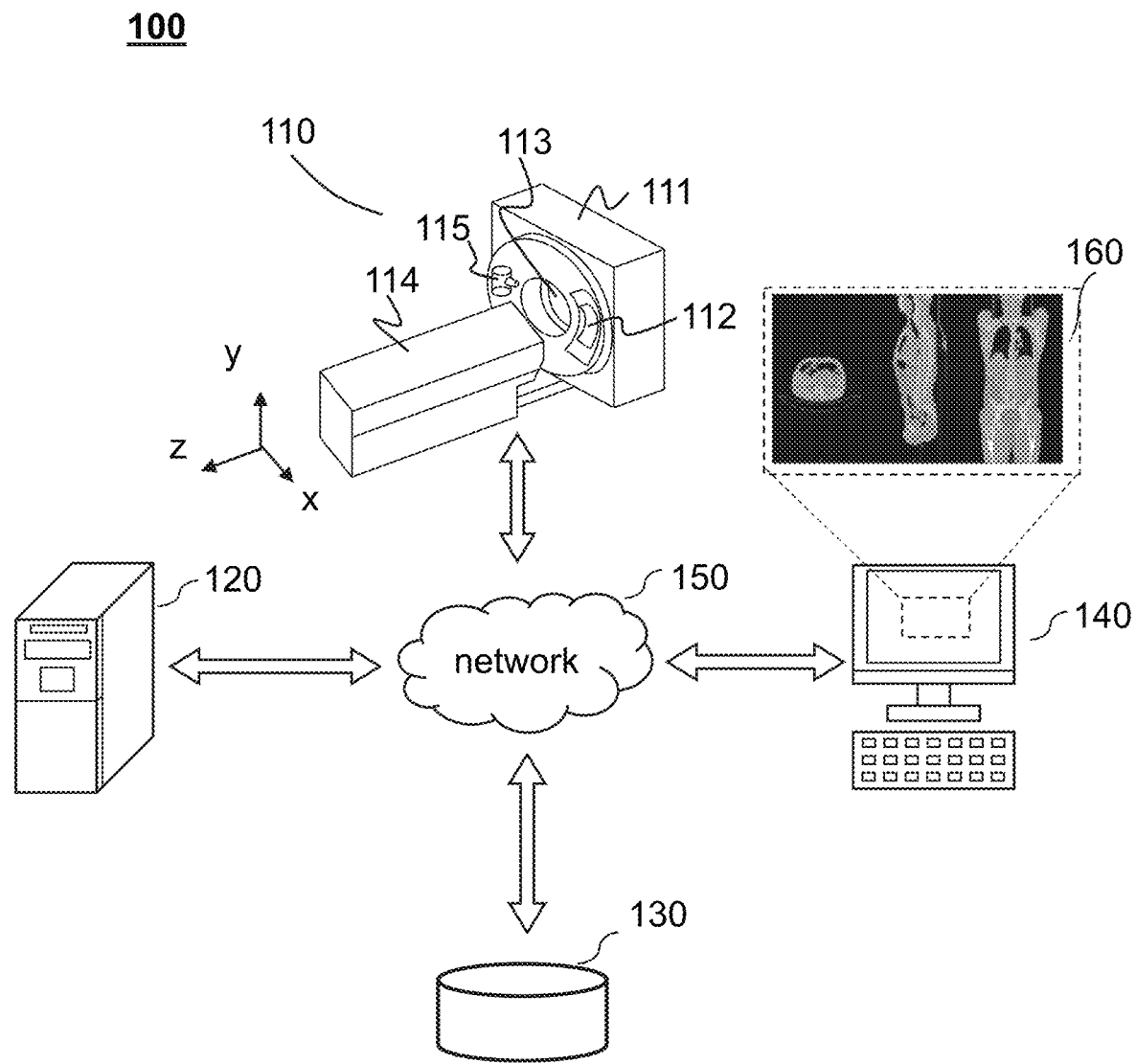
FIG. 1 is a schematic diagram illustrating an exemplary imaging system 100 according to some embodiments of the present disclosure.

FIG. 1 is a schematic diagram illustrating an exemplary imaging system 100 according to some embodiments of the present disclosure. The imaging system 100 may include a CT scanner 110, a processing apparatus 120, a storage device 130, a terminal device 140, and a network 150.

The CT scanner 110 may include a gantry 111, a detector 112, a detecting region 113, a table 114, and a radioactive scanning source 115. The gantry 111 may support the detector 112 and the radioactive scanning source 115. A subject (e.g., a patient) may be placed on the table 114 for scanning. The radioactive scanning source 115 may emit radioactive rays to the subject. The detector 112 may detect radiations (e.g., gamma photons) emitted from the detecting region 113. In some embodiments, the detector 112 may include one or more detector units. The detector unit may be and/or include a single-row detector and/or a multi-rows detector.

The processing apparatus 120 may process data and/or information acquired from the CT scanner 110, the storage device 130, and/or the terminal device 140. For example, the processing apparatus 120 may process acquired data, and reconstruct a CT image based on the processed data. In some embodiments, the processing apparatus 120 may be a computer, a user console, a single server, a server group, etc. The server group may be centralized or distributed. In some embodiments, the processing apparatus 120 may be local or remote. For example, the processing apparatus 120 may access information and/or data stored in the CT scanner 110, the terminal device 140, and/or the storage device 130 via the network 150. As another example, the processing apparatus 120 may be directly connected to the CT scanner 110, the terminal device 140 and/or the storage device 130 to access stored information and/or data. In some embodiments, the processing apparatus 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing apparatus 120 may be implemented by a computing device 200 having one or more components as illustrated in FIG. 2.

The storage device 130 may store data, instructions, and/or any other information. In some embodiments, the storage device 130 may store data obtained from the CT scanner 110, the terminal device 140 and/or the processing apparatus 120. In some embodiments, the storage device 130 may store data and/or instructions that the processing apparatus 120 may execute or use to perform exemplary methods described in the present disclosure. In some embodiments, the storage device 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing apparatus 120, the terminal device 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing apparatus 120, the terminal device 140, etc.). In some embodiments, the storage device 130 may be part of the processing apparatus 120.

The terminal device 140 may input/output signals, data, information, etc. In some embodiments, the terminal device 140 may enable a user interaction with the processing apparatus 120. For example, the terminal device 140 may display a reconstructed CT image on a screen 160. The terminal device 140 may be a desktop computer, a tablet computer, a laptop computer, a mobile device, or the like, or any combination thereof. In some embodiments, the mobile device may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 140 may be part of the processing apparatus 120.

The network 150 may include any suitable network that can facilitate exchange of information and/or data for the imaging system 100. In some embodiments, one or more components of the imaging system 100 (e.g., the CT scanner 110, the terminal device 140, the processing apparatus 120, the storage device 130, etc.) may communicate information and/or data with one or more other components of the imaging system 100 via the network 150. For example, the processing apparatus 120 may obtain CT data from the CT scanner 110 via the network 150. As another example, the processing apparatus 120 may obtain user instructions from the terminal device 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

FIG. 2 is a schematic diagram illustrating exemplary components of a computing device according to some embodiments of the present disclosure. The CT scanner 110, the processing apparatus 120, the storage device 130, and/or the terminal device 140 may be implemented on the computing device 200 according to some embodiments of the present disclosure. The particular system may use a functional block diagram to explain the hardware platform containing one or more user interfaces. The computer may be a computer with general or specific functions. Both types of the computers may be configured to implement any particular system according to some embodiments of the present disclosure. Computing device 200 may be configured to implement any components that perform one or more functions disclosed in the present disclosure. For example, the computing device 200 may implement any component of the imaging system 100 as described herein. In FIGS. 1-2, only one such computer device is shown purely for convenience purposes. One of ordinary skill in the art would have understood at the time of filing of this application that the computer functions relating to the imaging as described herein may be implemented in a distributed fashion on a number of similar platforms, to distribute the processing load.

The computing device 200, for example, may include COM ports 250 connected to and from a network connected thereto to facilitate data communications. The computing device 200 may also include a processor (e.g., the central processing unit (CPU) 220), in the form of one or more processors (e.g., logic circuits), for executing program instructions. For example, the processor may include interface circuits and processing circuits therein. The interface circuits may be configured to receive electronic signals from a bus 210, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the bus 210.

The exemplary computing device may include the internal communication bus 210, program storage and data storage of different forms including, for example, a disk 270, and a read only memory (ROM) 230, or a random access memory (RAM) 240, for various data files to be processed and/or transmitted by the computing device. The exemplary computing device may also include program instructions stored in the ROM 230, RAM 240, and/or other type of non-transitory storage medium to be executed by the processor 220. The methods and/or processes of the present disclosure may be implemented as the program instructions. The computing device 200 also includes an I/O component 260, supporting input/output between the computer and other components. The computing device 200 may also receive programming and data via network communications.

Merely for illustration, only one processor and/or processor is illustrated in FIG. 2. Multiple CPUs and/or processors are also contemplated; and thus, operations and/or method steps performed by one CPU and/or processor as described in the present disclosure may also be jointly or separately performed by the multiple CPUs and/or processors. For example, if in the present disclosure the CPU and/or processor of the computing device 200 executes both step A and step B, it should be understood that step A and step B may also be performed by two different CPUs and/or processors jointly or separately in the computing device 200 (e.g., the first processor executes step A and the second processor executes step B, or the first and second processors jointly execute steps A and B).

Figure 3:
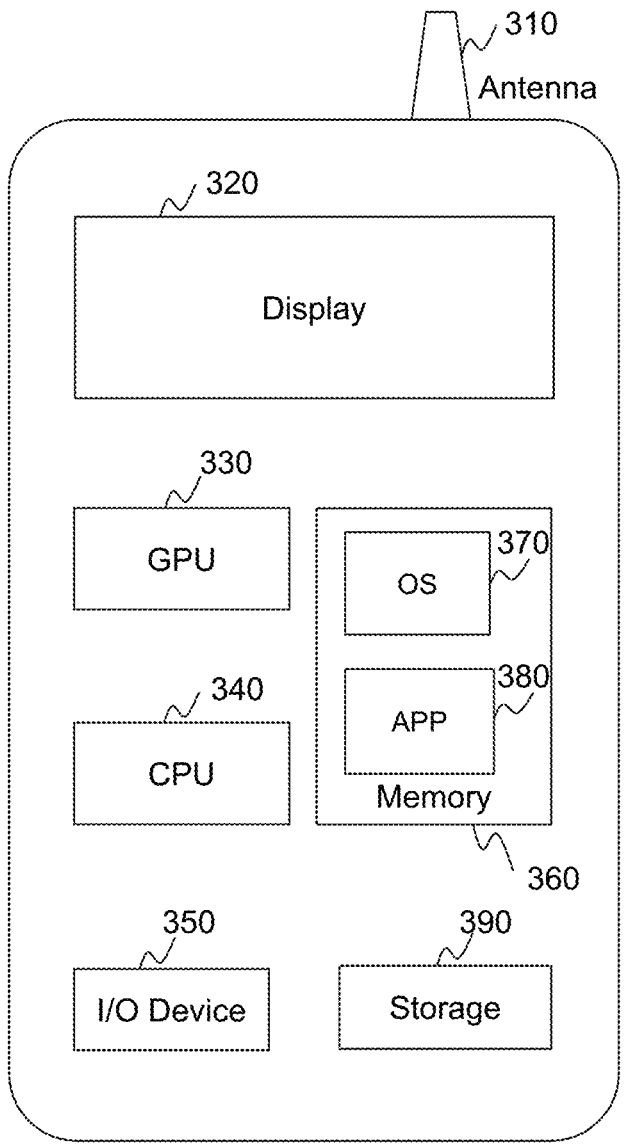
FIG. 3 is a block diagram illustrating exemplary hardware and/or software components of an exemplary requestor terminal according to some embodiments of the present disclosure.

FIG. 3 is a block diagram illustrating exemplary hardware and/or software components of an exemplary requestor terminal according to some embodiments of the present disclosure. The terminal device 130 may be implemented on the mobile device 300 according to some embodiments of the present disclosure. As illustrated in FIG. 3, the mobile device 300 may include an antenna 310, a display 320, a graphic processing unit (GPU) 330, a central processing unit (CPU) 340, an I/O device 350, a memory 360, and a storage 390. The CPU 340 may include interface circuits and processing circuits similar to the processor 220. In some embodiments, any other suitable component, including but not limited to a system bus or a controller (not shown), may also be included in the mobile device 300. In some embodiments, a mobile operating system 370 (e.g., iOS™, Android™ Windows Phone™, etc.) and one or more applications 380 may be loaded into the memory 360 from the storage 390 in order to be executed by the CPU 340. The applications 380 may include a browser or any other suitable mobile apps for receiving and rendering information relating to CT data processing or other information from the imaging system on the mobile device 300. User interactions with the information stream may be achieved via the I/O device 350 and provided to the processing apparatus 120 and/or other components of the imaging system 100 via the network 150.

In order to implement various modules, units and their functions described above, a computer hardware platform may be used as hardware platforms of one or more elements (e.g., a component of the sever 110 described in FIG. 1). Since these hardware elements, operating systems, and program languages are common, it may be assumed that persons skilled in the art may be familiar with these techniques and they may be able to provide information required in the data classification according to the techniques described in the present disclosure. A computer with user interface may be used as a personal computer (PC), or other types of workstations or terminal devices. After being properly programmed, a computer with user interface may be used as a server. It may be considered that those skilled in the art may also be familiar with such structures, programs, or general operations of this type of computer device. Thus, extra explanations are not described for the figures.

Figure 4A:
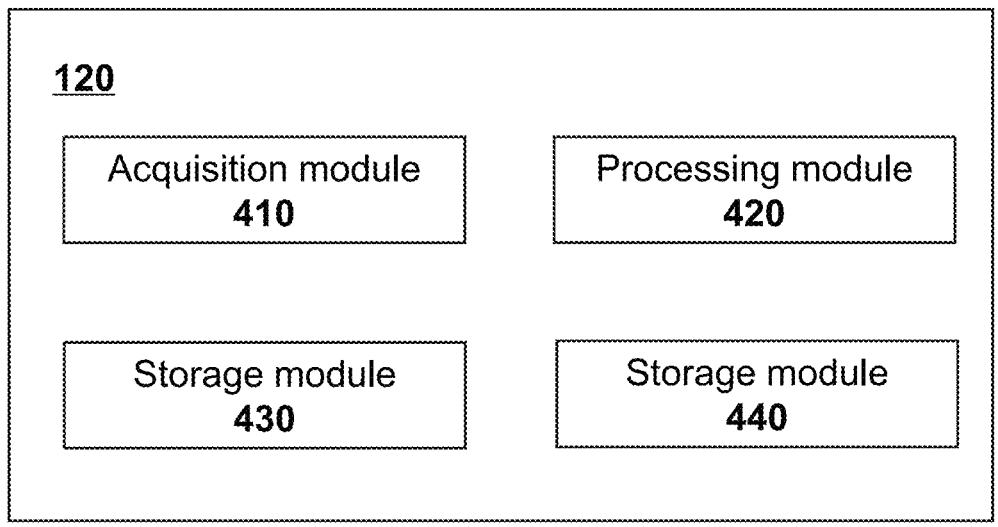
FIG. 4A is a block diagram illustrating an exemplary processing apparatus 120 according to some embodiments of the present disclosure.

FIG. 4A is a block diagram illustrating an exemplary processing apparatus 120 according to some embodiments of the present disclosure. As illustrated in FIG. 4, the processing apparatus 120 may include an acquisition module 410, a processing module 420, a storage module 430, and a communication module 440.

The acquisition module 410 may acquire data. The acquisition module 410 may acquire data from the CT scanner 110, the storage device 130, the terminal device 140, or any devices or components capable of storing data via the network 150. For example, the acquisition module 410 may acquire data from a medical cloud data center (not shown) via the network 150. The acquired data may include original CT data, processing results (e.g., processed CT data, CT images), user instructions, algorithms, program codes, or the like, or a combination thereof. As used herein, the original CT data refers to CT data obtained from the CT scanner 110 without further processing. In some embodiments, the acquisition module 410 may acquire original CT data from the CT scanner 110, more particularly, from the CT detector 112. The acquisition module 410 may transmit the acquired data to a storage device (e.g., the storage module 430, the storage device 130, etc.) for storage. The CT data may be stored in forms of pixel information, voxel information, images, vectors, or the like, or any combination thereof. In some embodiments, the acquisition module 410 may transmit the acquired data to a computing device (e.g., the processing module 420) for processing.

The processing module 420 may process data provided by various modules or components of the imaging system 100. For example, the processing module 420 may process CT data acquired by the acquisition module 410, or retrieved from the storage module 430, etc. The processing module 420 may process the obtained data by performing a plurality of operations. Exemplary data processing operations may include data correction, data conversion, normalization, image reconstruction, etc. In some embodiments, the processing module 420 may determine a data correction algorithm, and correct original CT data based on the data correction algorithm. For example, the processing module 420 may obtain a data correction algorithm for removing a signal of the table 114 from the original CT data, and correct the original CT data based on the data correction algorithm. In some embodiments, the processing module 420 may determine a data conversion coefficient or function, and convert obtained data into another format. For example, the processing module 420 may convert original CT data represented by grey scale values into CT values using a function. In some embodiments, the processing module 420 may reconstruct CT images, based on the original CT data and/or the processed CT data, according to a reconstruction algorithm, generate reports including one or more CT images and/or other related information, and/or perform any other function for image reconstruction in accordance with various embodiments of the present disclosure. Exemplary image reconstruction algorithms may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

The storage module 430 may store data. Merely by ways of example, the storage module 430 may store original CT data, processed CT data, control parameters, data processing algorithms, or the like, or a combination thereof. In some embodiments, the storage module 430 may store one or more programs and/or instructions that may be executed by the processor(s) of the processing apparatus 120 to perform exemplary methods described in this disclosure. For example, the storage module 430 may store a program for the processing apparatus 120 to reconstruct an image of an intervertebral of a spine of a subject.

The storage module 430 may be or include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc.

The communication module 440 may be connected to a network (e.g., the network 150) to facilitate data communications. The communication module 440 may establish connections between the processing apparatus 120 and the CT scanner 110, storage device 130 and/or the terminal device 140. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication module 440 may be and/or include a standardized communication port, such as RS232, RS485, etc. In some embodiments, the communication module 440 may be a specially designed communication port. For example, the communication module 440 may be designed in accordance with the digital imaging and communications in medicine (DICOM) protocol.

It should be noted that the above description of the processing apparatus 120 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more modules illustrated in FIG. 4 may be implemented in at least part of the exemplary imaging system 100 as illustrated in FIG. 1. For example, the acquisition module 410, the processing module 420, the storage module 430, and/or the communication module 440 may be integrated into a console (not shown). Via the console, a user may set parameters for scanning a subject, controlling imaging processes, correcting CT data, controlling parameters for reconstruction of an image, viewing reconstructed images, etc.

Figure 4B:
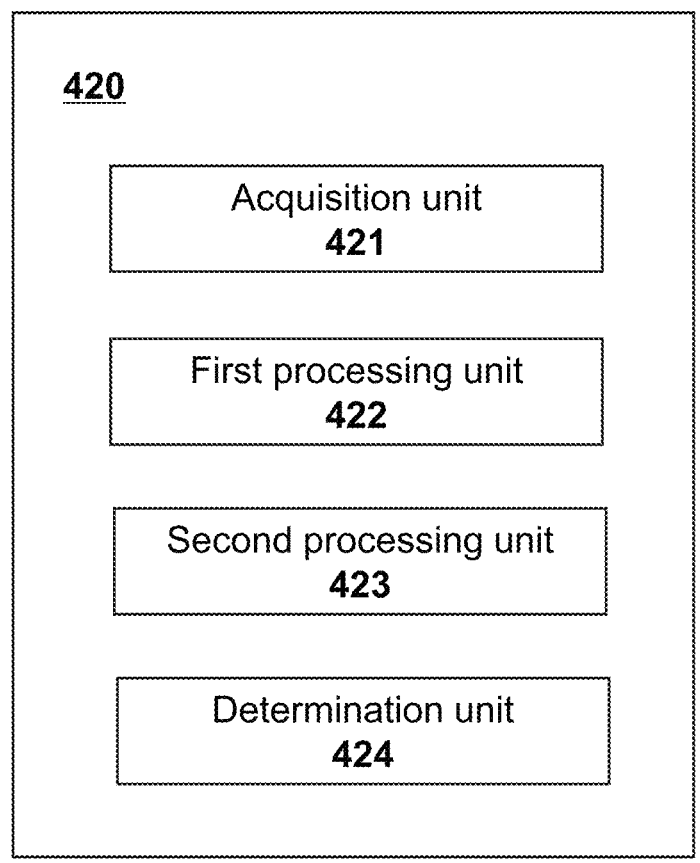
FIG. 4B is a block diagram illustrating an exemplary processing module 420 according to some embodiments of the present disclosure.

FIG. 4B is a block diagram illustrating an exemplary processing module 420 according to some embodiments of the present disclosure. The processing module 420 may include an acquisition unit 421, a first processing unit 422, a second processing unit 423, a determination unit 424, and a reconstruction unit 425. The one or more units in the processing module 420 may be implemented on various components (e.g., the CPU 220 of the computing device 200 as illustrated in FIG. 2) in the present disclosure.

The acquisition unit 421 may obtain CT data or CT images. In some embodiments, the CT data/images may be original CT data/images. The CT data may be original CT data acquired from the CT scanner 110 by scanning a subject. The CT image may be original CT image. An original CT image may be an image or image data. In some embodiments, each of the plurality of original CT images may be a two-dimensional (2D) image or 2D image data. Merely by ways of example, each original CT image may be a 2D grey scale image. In some embodiments, the plurality of original CT images may constitute a three-dimensional (3D) image or 3D image data of the spine of the subject. In some embodiments, In some embodiments, the CT data/images may be processed CT data/images. For example, the CT data/images may be processed by removing artifacts (e.g., a signal of a bed supporting an imaged subject).

The first processing unit 422 may identify an optimal sagittal image may be identified. The optimal sagittal image may be a sagittal image showing a sagittal morphological structure of a spine of a subject. The first processing unit 422 may obtain one or more original CT images from the acquisition unit 421, and convert the original CT images into CT value images. The original CT images may be grey scale images. Each pixel of a grey scale image may have a grey scale value in a range of 0-255 or 0-4096 in compliance with DICOM. The first processing unit 422 may convert the grey scale value of each pixel of the grey scale image into a CT value according to a predetermined algorithm. The first processing unit 422 may determine a first CT value, which may be used as a threshold to separate bones from soft tissues in CT value images. The first processing unit 422 may applying the first CT value to the CT value images to generate first binary images of the spine. The first processing unit 422 may compare a CT value of each pixel in the CT value images with the first CT value. If the CT value of the pixel in the CT value images is larger than or equal to the first CT value, the CT value of the pixel may be set to a first value (e.g., 1). If the CT value of the pixel in the CT value images is smaller than the first CT value, the CT value of the pixel may be set to a second value (e.g., 0).

Then the first processing unit 422 may form a 2D summed image by summing the first binary images. The operation that summing the first binary images corresponding to the plurality of original CT images may also be referred to as "pixel addition". The 2D summed image may have an extreme point. The extreme point may be a pixel among pixels of the 2D summed image which has a maximum value.

The first processing unit 422 may determine the optimal sagittal image based on the extreme point in the 2D summed image. The 2D summed image may be in the x-y plane. The first processing unit 422 may determine an image of the spine in the y-z plane including the extreme point. Since the determined image is in the y-z plane and includes the extreme point, the first processing unit 422 may designate the determined image as the optimal sagittal image.

The second processing unit 423 may identify a centerline of the spine within the optimal sagittal image. The second processing unit 423 may obtain the optimal sagittal image from the first processing unit 422, and identify the centerline of the spine (also referred to as "spine centerline") within the optimal sagittal image. A set of sagittal images located within a specified distance from the optimal sagittal image may be selected. The set of sagittal images may be parallel to the optimal sagittal image. Then a 2D minimum density projection image may be generated by applying a minimum density projection (MinIP) algorithm to the set of selected sagittal images. The 2D minimum density projection image may be segmented using a threshold, for example, a second CT value, to generate a second binary image. Since bones in the second binary image are separated, a morphological dilation operation may be performed to connect bones in the second binary image into a connected region, thus a dilated map may be generated. For example, since adjacent bones of the spine may be separated by intervertebral discs, the separated bones may be connected using the morphological dilation operation. Further, a maximum connected region in the dilated map may be determined.

Holes between or within connected regions in the dilated map may be removed or eliminated by performing a morphological closing operation. In some embodiments, the second processing unit 423 may perform the morphological closing operation using a structon. In some embodiments, a circular structon with a radius larger than the thickness of an intervertebral disc may be selected. Merely for illustration purposes, the circular structon may have a radius of 8/p, where p denotes the thickness of a cross-sectional image. The circular structon may move along a preliminary centerline of the spine at a preset step length (e.g., 30 millimeter) and perform a mean-value smoothing on the preliminary centerline.

In some embodiments, a set of center points may be determined after the second processing unit 423 performs the mean-value smoothing on the preliminary centerline with the circular structon. The set of center points may be on the spine centerline, and the second processing unit 423 may determine the spine centerline by connecting the set of center points sequentially.

The determination unit 424 may determine a center point and a direction of at least one intervertebral disc based on the identified spine centerline. The determination unit 424 may obtain the dilated map with identified spine centerline from the second processing unit 423, and determine the center point and the direction of at least one intervertebral disc based on the dilated map with the identified spine centerline. A point-direction-mean value set of the spine centerline may be determined. The point-direction-mean value set may include a plurality of elements. Each element may represent a point on the spine centerline, which includes a mean value associated with the point, and a direction associated with the point.

The determination unit 424 may determine each element of the point-direction-mean value set based on the dilated map including the spine centerline. In some embodiments, for a point (i.e., a center point) on the spine centerline, a straight line being in a certain direction (e.g., perpendicular to the spine centerline in the y-z plane) that passes through the point may be determined. The straight line may intersect with the outline of the spine represented by the maximum connected region at two points. The determination unit 424 may select pixels along the straight line between the two points, and obtain values of the pixels on the straight line. In some embodiments, a mean value associated with the straight line may be determined by determining an average value of the obtained values of the pixels. In some embodiments, a set of straight lines may be determined by rotating the straight line around the point at a preset step each time. For example, the determination unit 424 may rotate the straight line around the point at a step of 1 degrees each time, and determine the set of straight lines after the straight line is rotated over 30 degrees. Similarly, mean values associated with the straight lines may be determined. Then the determination unit 424 may identify a minimum mean value from the mean values associated with the straight lines in different directions that pass through the point on the spine centerline. In some embodiments, the minimum mean value may be designated as a mean value associated with the point. In some embodiments, the direction of the straight line corresponding to the minimum mean value may be designated as the direction associated with the point. The point, the mean value associated with the point, and the direction associated with the point may constitute an element of the point-direction-mean value set related to the point.

The determination unit 424 may identify the plurality of center points on the spine centerline, and determine the point-direction-mean value set S by determining each element of the point-direction-mean value set related to a point of the plurality of center points on the spine centerline.

Then a point on the spine centerline corresponding to each of the at least one intervertebral disc may be determined using the point-direction-mean value set of the spine centerline. In some embodiments, the determination unit 424 may determine, based on the point-direction-mean value set of the spine centerline, a point-mean value curve represented in a schematic diagram. The point-mean value curve may have a plurality of nadirs. Each nadir of the point-mean value curve may correspond to an intervertebral disc center. The intervertebral disc center in the thickness direction herein refers to a line segment crossing the center of the intervertebral disc in the thickness direction. The line segment may include a plurality of points on the intervertebral disc center.

The center point and the direction of the at least one intervertebral disc may be determined. The direction of the at least one intervertebral disc refers to a direction perpendicular to the thickness direction of the at least one intervertebral disc. The center point of an intervertebral disc refers to a geometric center point of the intervertebral disc on the intervertebral disc center. Since the intervertebral disc center of each intervertebral disc is a line segment including a plurality of points on the intervertebral disc center, the plurality of points on each intervertebral disc center may be determined by checking the index corresponding to each nadir of the point-mean value curve. In some embodiments, the determination unit 424 may determine coordinates of the plurality of points on an intervertebral disc center, and determine a center point of the intervertebral disc based on the coordinates of the plurality of points and the point-direction-mean value set. Merely by ways of example, the determination unit 424 may determine mean values of x coordinates and y coordinates of the plurality of points, and designate the mean value of the x coordinates of the plurality of points as the x coordinate of the center point of the intervertebral disc and the mean value of the y coordinates of the plurality of points as the y coordinate of the center point of the intervertebral disc. In some embodiments, the determination unit 424 may determine directions of the plurality of points on an intervertebral disc center, and determine a direction of the intervertebral disc based on the directions of the plurality of points and the point-direction-mean value set. Merely by ways of example, the determination unit 424 may determine a mean value of directions of the plurality of points, and designate the mean value as the direction of the intervertebral disc.

It should be noted that the above description of the processing module 420 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, at least one of the plurality of units in the processing module 420 may include a storage unit (not shown). As another example, any one of the plurality of units in the processing module 420 may be divided into two or more sub-units or blocks.

Figure 4C:
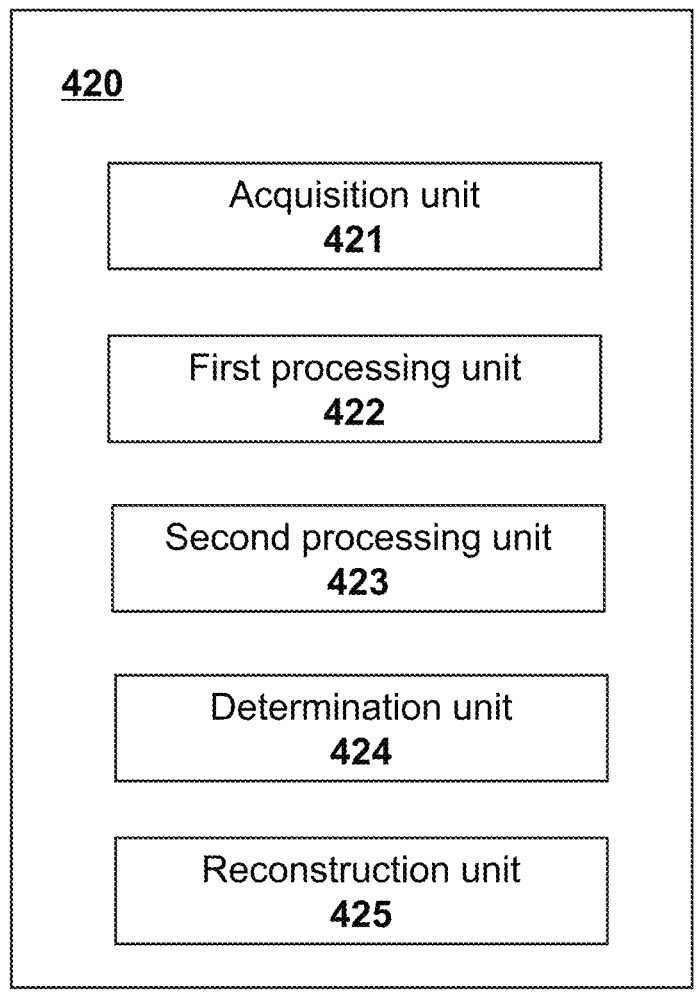
FIG. 4C is a block diagram illustrating an exemplary processing module 420 according to some embodiments of the present disclosure.

FIG. 4C is a block diagram illustrating an exemplary processing module 420 according to some embodiments of the present disclosure. The processing module 420 may further include a reconstruction unit 425 in comparison with FIG. 4B. The reconstruction unit 425 may reconstruct CT images of a subject. In some embodiments, the reconstruction unit 425 may reconstruct original CT images based on original CT data acquired by scanning a subject. In some embodiments, the reconstruction unit 425 may reconstruct CT images based on processed CT data. For example, since the center points and orientations of one or more intervertebral discs are identified, the planes on which the one or more intervertebral discs are located may be determined. The reconstruction unit 425 may generate images of one or more intervertebral discs by reconstructing the images of the planes.

In some embodiments, the reconstruction unit 425 may use various image reconstruction techniques to reconstruct the images of the planes. Exemplary image reconstruction techniques may include multiple planar reconstruction, iterative reconstruction (e.g., statistical reconstruction), Fourier slice theorem, filtered back projection (FBP), fan-beam reconstruction, analytic reconstruction, or the like, or any combination thereof.

Figure 5:
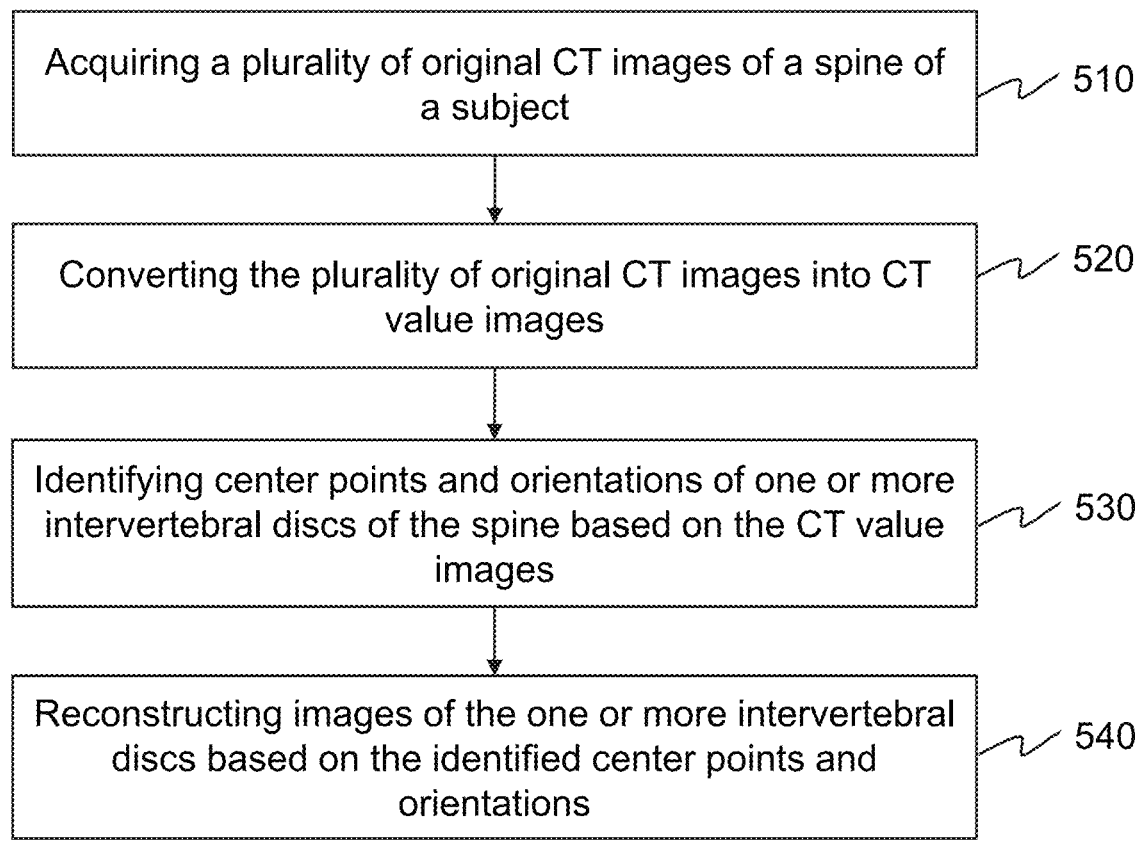
FIG. 5 is a flowchart illustrating an exemplary process for reconstructing an image of at least one intervertebral disc of a spine of a subject according to some embodiments of the present disclosure.

FIG. 5 is a flowchart illustrating an exemplary process for reconstructing an image of at least one intervertebral disc of a spine of a subject according to some embodiments of the present disclosure. In some embodiments, the process 500 may be executed by the processing module 420. For example, the process 500 may be implemented as a set of instructions stored in the storage device 130, and/or the storage module 430. The processing apparatus 120 and/or the CPU 220 may execute the set of instructions and may accordingly be directed to perform the process 500.

Figure 10A:
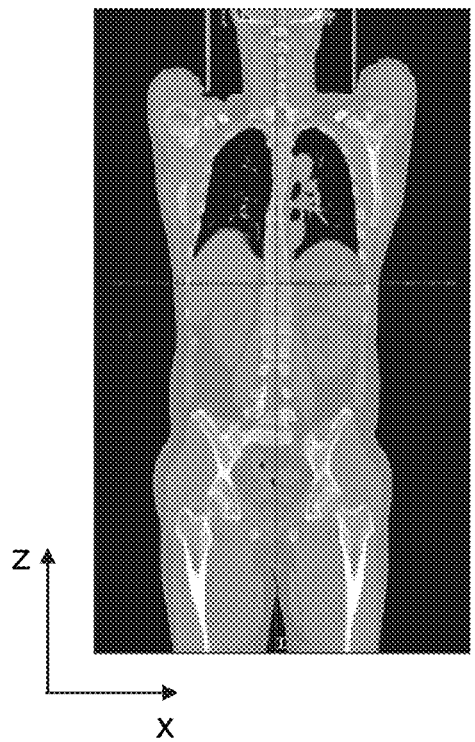
FIGS. 10A-10C illustrates exemplary views of a spine of a patient generated based on original CT images according to some embodiments of the present disclosure.
Figure 10B:
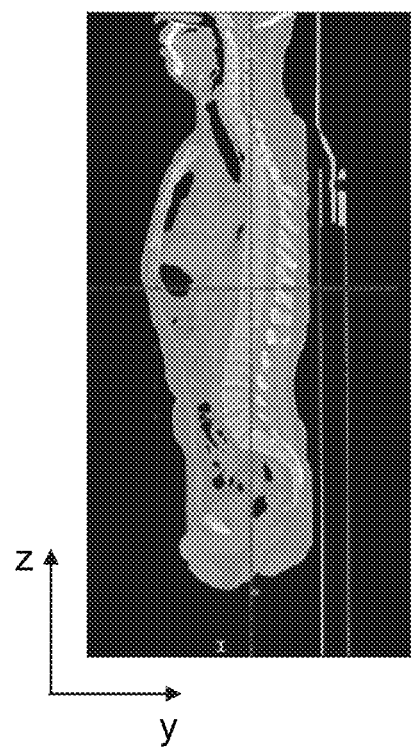
Figure 10C:
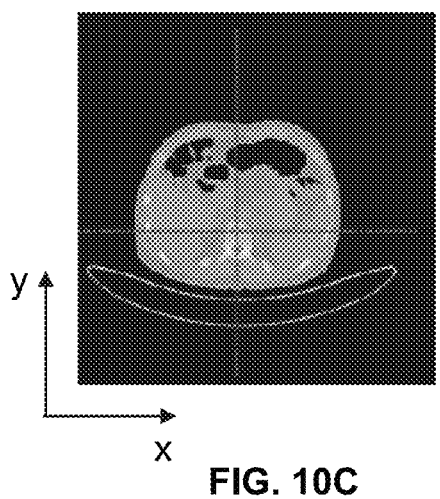

In 510, a plurality of original CT images of a spine of a subject may be acquired. As used herein, the plurality of original CT images refer to images reconstructed based on original CT data. In some embodiments, the plurality of original CT images may be slices in a predetermined sequence generated by the imaging system 100 after the imaging system 100 scans the subject along a predetermined direction, for example, from the head to the feet of the subject. In some embodiments, the plurality of original CT images may be transmitted, in accordance with the predetermined sequence, to a designated device so as to obtain different views of the spine of the subject including a coronal view, a sagittal view, and/or a cross-sectional view as illustrated in FIGS. 10A-10C.

An original CT image may be an image or image data. In some embodiments, each of the plurality of original CT images may be a two-dimensional (2D) image or 2D image data. Merely by ways of example, each original CT image may be a 2D grey scale image. In some embodiments, the plurality of original CT images may constitute a three-dimensional (3D) image or 3D image data of the spine of the subject.

The original CT images may be acquired by, for example, the acquisition unit 421. In some embodiments, the acquisition unit 421 may acquire the original CT images from a storage device (e.g., the storage device 130, the disk 270, the storage 390, etc.). In some embodiments, the acquisition unit 421 may acquire the original CT images from the processing module 420. For example, the processing module 420 may reconstruct the original CT images based on original CT data acquired by scanning the subject. More particularly, the imaging system 100 may acquire the original CT data by scanning the subject along the z-direction as illustrated in FIG. 1, and reconstruct multiple CT images based on the original CT data. The multiple CT images may be 2D images (also referred to as "slices") which are perpendicular to the z-direction. In some embodiments, at least a part of the multiple CT images may be designated as the plurality of original CT images of the spine of the subject.

In some embodiments, the plurality of original CT images may be transmitted, according to the predetermined sequence, to a designated device or component, for example, the processing apparatus 120 of the imaging system or a work station (not shown) connected to the imaging system 100 via the network 150. The designated device or component may generate different views (e.g., a coronal view, a sagittal view, or a cross-sectional view) of the spine of the subject based on the plurality of original CT images. Merely for illustration purposes, FIGS. 10A-10C illustrate exemplary views of a spine of a patient generated based on original CT images according to some embodiments of the present disclosure. The original CT images may include multiple views of slices being perpendicular to a direction from the head to the feet of the patient, i.e., z-direction shown in FIG. 1. As illustrated in FIGS. 10A-10C, the exemplary views may include a coronal view (shown in FIG. 10A, which is also referred to as "coronal image"), a sagittal view (shown in FIG. 10B, which is also referred to as "sagittal image"), and a cross-sectional view (shown in FIG. 10C, which is also referred to as "cross-sectional image").

In 520, the plurality of original CT images may be converted into CT value images. In some embodiments, the original CT images may be converted into the CT value images by the first processing unit 422.

An original CT image may include a signal of a table (e.g., the table 114) since the subject is placed on the table when the CT scanner 110 scans the subject. The signal of the table may influence the imaging of the spine. Thus, the original CT image may be preprocessed to remove the signal of the table before the original CT image is further processed (e.g., converted into the CT value image).

In some embodiments, the imaging system 100 may obtain a preprocessing algorithm which may reduce or eliminate the influence of the table during imaging. Each of the plurality of original CT images may be preprocessed using the preprocessing algorithm. In some embodiments, the imaging system 100 may obtain the signal of the table by scanning the table when the subject is not on the table, and preprocess the original CT image by subtracting the signal of the table from the original CT images.

In some embodiments, the original CT images may be grey scale images. Each pixel of a grey scale image may have a grey scale value in a range of 0-255 or 0-4096 in compliance with DICOM. The first processing unit 422 may convert the grey scale value of each pixel of the grey scale image into a CT value according to a predetermined algorithm. For example, the first processing unit 422 may obtain tag information of each pixel, and convert the grey scale value of each pixel of the grey scale image into a CT value based on the tag information. The tag information may include a rescale intercept and a rescale slope.

In 530, center points and orientations of one or more intervertebral discs of the spine may be identified based on the CT value images. In some embodiments, the center points and orientations of the intervertebral discs of the spine may be identified by the determination unit 424. An intervertebral disc refers to fibrocartilage between adjacent vertebrae in the spine of the subject. To reconstruct an image of an intervertebral disc, a plane on which the intervertebral disc is located (i.e., a position of the intervertebral disc) may need to be determined based on the CT value images. In some embodiments, the determination unit 424 may determine the plane by identifying a center point and an orientation (also referred to as "direction") of the intervertebral disc of the spine based on the CT value images. Details regarding the identification of the center points and orientations of the one or more intervertebral discs of the spine may be disclosed elsewhere in the present disclosure, for example, FIGS. 6 through 9, and the descriptions thereof.

In 540, images of the one or more intervertebral discs may be reconstructed based on the identified center points and orientations. The images may be reconstructed by, for example, the reconstruction unit 425. Since the center points and orientations of the one or more intervertebral discs are identified, the planes on which the one or more intervertebral discs are located may be determined. The reconstruction unit 425 may generate images of the one or more intervertebral discs by reconstructing the images of the planes. In some embodiments, various image reconstruction techniques may be used to reconstruct the images of the planes. Exemplary image reconstruction techniques may include multiple planar reconstruction, iterative reconstruction (e.g., statistical reconstruction), Fourier slice theorem, filtered back projection (FBP), fan-beam reconstruction, analytic reconstruction, or the like, or any combination thereof.

It should be noted that the above description of the process 500 is provided for the purposes of illustration, not intended to limit the scope of the present disclosure. For persons having ordinary skills in the art, multiple variations and modifications may be reduced to practice in the light of the present disclosure. For example, the operations in the process 500 may be implemented in a magnetic resonance imaging (MRI) system, a computed tomography-positron emission tomography (CT-PET) system, an emission computed tomography (ECT) system, a computed tomography-magnetic resonance imaging (CT-MRI) system, an ultrasonography system, an X-ray photography system, or the like, or any combination thereof. As another example, the process 500 may further include an operation for storing the images of the one or more intervertebral discs of the spine generated by performing an optimal multi-planar reconstruction. However, these variations and modifications fall in the scope of the present disclosure.

Figure 6:
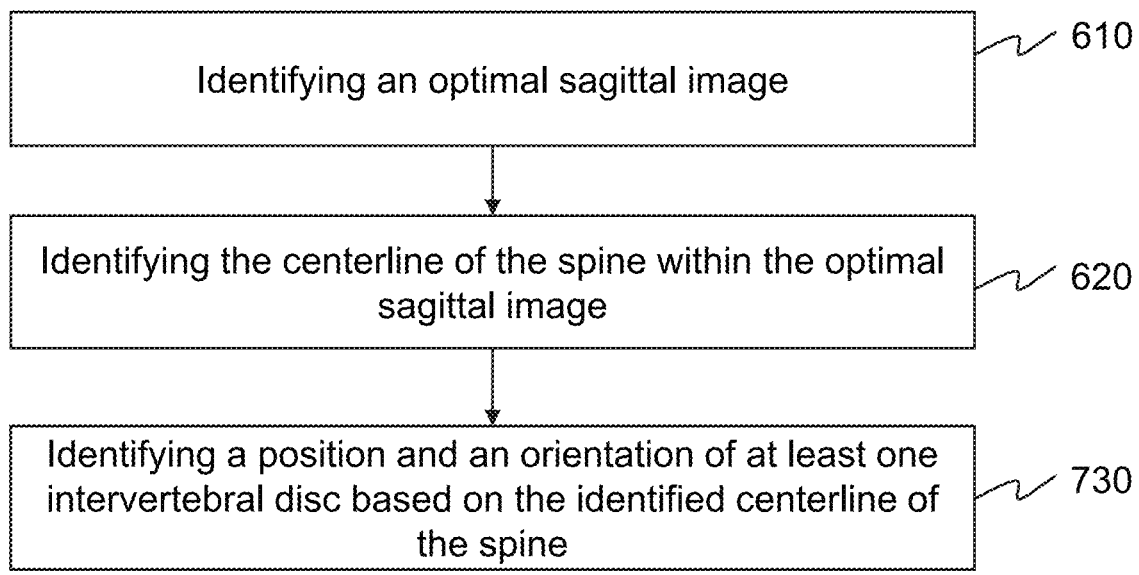
FIG. 6 is a flowchart illustrating an exemplary process for identifying a center point and an orientation of an intervertebral disc according to some embodiments of the present disclosure.

FIG. 6 is a flowchart illustrating an exemplary process for identifying a center point and an orientation of an intervertebral disc according to some embodiments of the present disclosure. In some embodiments, the process 600 may be executed by the processing module 420. For example, the process 600 may be implemented as a set of instructions stored in the storage device 130, and/or the storage module 430. The processing apparatus 120 and/or the CPU 220 may execute the set of instructions and may accordingly be directed to perform the process 600.

In 610, an optimal sagittal image may be identified. In some embodiments, the optimal sagittal image may be identified by the first processing unit 422. The optimal sagittal image. A first CT value may be determined. The first CT value may be a threshold used to separate bones from soft tissues in CT value images generated by scanning a spine of a subject. The first processing unit 422 may applying the first CT value to the CT value images to generate first binary images of the spine. The imaging system 100 may compare a CT value of each pixel in the CT value images with the first CT value. If the CT value of the pixel in the CT value images is larger than or equal to the first CT value, the CT value of the pixel may be set to a first value (e.g., 1). If the CT value of the pixel in the CT value images is smaller than the first CT value, the CT value of the pixel may be set to a second value (e.g., 0).

Then the first processing unit 422 may form a 2D summed image by summing the first binary images. The operation that summing the first binary images corresponding to the plurality of original CT images may also be referred to as "pixel addition". The 2D summed image may have an extreme point. The extreme point may be a pixel among pixels of the 2D summed image which has a maximum value.

The first processing unit 422 may determine the optimal sagittal image based on the extreme point in the 2D summed image. The 2D summed image may be in the x-y plane. The first processing unit 422 may determine an image of the spine in the y-z plane including the extreme point. Since the determined image is in the y-z plane and includes the extreme point, the first processing unit 422 may designate the determined image as the optimal sagittal image. Detail regarding the identification of the optimal sagittal image may be disclosed elsewhere in the present disclosure, for example, FIG. 7, and the descriptions thereof.

In 620, the centerline of the spine may be identified within the optimal sagittal image. In some embodiments, the centerline of the spine may be identified by the second processing unit 423. A set of sagittal images located within a specified distance from the optimal sagittal image may be selected. The set of sagittal images may be parallel to the optimal sagittal image. Then a 2D minimum density projection image may be generated by applying a minimum density projection (MinIP) algorithm to the set of selected sagittal images. The 2D minimum density projection image may be segmented using a threshold, for example, a second CT value, to generate a second binary image. Since bones in the second binary image are separated, a morphological dilation operation may be performed to connect bones in the second binary image into a connected region, thus a dilated map may be generated. For example, since adjacent bones of the spine may be separated by intervertebral discs, the separated bones may be connected using the morphological dilation operation. Further, a maximum connected region in the dilated map may be determined.

Holes between or within connected regions in the dilated map may be removed or eliminated by performing a morphological closing operation. In some embodiments, the second processing unit 423 may perform the morphological closing operation using a structon. In some embodiments, a circular structon with a radius larger than the thickness of an intervertebral disc may be selected. Merely for illustration purposes, the circular structon may have a radius of 8/p, where p denotes the thickness of a cross-sectional image. The circular structon may move along a preliminary centerline of the spine at a preset step length (e.g., 30 millimeter) and perform a mean-value smoothing on the preliminary centerline.

In some embodiments, a set of center points may be determined after the second processing unit 423 performs the mean-value smoothing on the preliminary centerline with the circular structon. The set of center points may be on the spine centerline, and the second processing unit 423 may determine the spine centerline by connecting the set of center points sequentially. Detail regarding the identification of the centerline of the spine within the optimal sagittal image may be disclosed elsewhere in the present disclosure, for example, FIG. 8, and the descriptions thereof.

In 630, a center point and a direction of at least one intervertebral disc may be determined based on the identified spine centerline. In some embodiments, the center point and the direction of the at least one intervertebral disc may be determined by the determination unit 424. A point-direction-mean value set of the spine centerline may be determined. The point-direction-mean value set may include a plurality of elements. Each element may represent a point on the spine centerline, which includes a mean value associated with the point, and a direction associated with the point.

The determination unit 424 may determine each element of the point-direction-mean value set based on the dilated map including the spine centerline. In some embodiments, for a point (i.e., a center point) on the spine centerline, a straight line being in a certain direction (e.g., perpendicular to the spine centerline in the y-z plane) that passes through the point may be determined. The straight line may intersect with the outline of the spine represented by the maximum connected region at two points. The determination unit 424 may select pixels along the straight line between the two points, and obtain values of the pixels on the straight line. In some embodiments, a mean value associated with the straight line may be determined by determining an average value of the obtained values of the pixels. In some embodiments, a set of straight lines may be determined by rotating the straight line around the point at a preset step each time. For example, the determination unit 424 may rotate the straight line around the point at a step of 1 degrees each time, and determine the set of straight lines after the straight line is rotated over 30 degrees. Similarly, mean values associated with the straight lines may be determined. Then the determination unit 424 may identify a minimum mean value from the mean values associated with the straight lines in different directions that pass through the point on the spine centerline. In some embodiments, the minimum mean value may be designated as a mean value associated with the point. In some embodiments, the direction of the straight line corresponding to the minimum mean value may be designated as the direction associated with the point. The point, the mean value associated with the point, and the direction associated with the point may constitute an element of the point-direction-mean value set related to the point.

The determination unit 424 may identify the plurality of center points on the spine centerline, and determine the point-direction-mean value set S by determining each element of the point-direction-mean value set related to a point of the plurality of center points on the spine centerline.

Then a point on the spine centerline corresponding to each of the at least one intervertebral disc may be determined using the point-direction-mean value set of the spine centerline. In some embodiments, the determination unit 424 may determine, based on the point-direction-mean value set of the spine centerline, a point-mean value curve represented in a schematic diagram. The point-mean value curve may have a plurality of nadirs. Each nadir of the point-mean value curve may correspond to an intervertebral disc center. The intervertebral disc center in the thickness direction herein refers to a line segment crossing the center of the intervertebral disc in the thickness direction. The line segment may include a plurality of points on the intervertebral disc center.

The center point and the direction of the at least one intervertebral disc may be determined. The direction of the at least one intervertebral disc refers to a direction perpendicular to the thickness direction of the at least one intervertebral disc. The center point of an intervertebral disc refers to a geometric center point of the intervertebral disc on the intervertebral disc center. Since the intervertebral disc center of each intervertebral disc is a line segment including a plurality of points on the intervertebral disc center, the plurality of points on each intervertebral disc center may be determined by checking the index corresponding to each nadir of the point-mean value curve. In some embodiments, the determination unit 424 may determine coordinates of the plurality of points on an intervertebral disc center, and determine a center point of the intervertebral disc based on the coordinates of the plurality of points and the point-direction-mean value set. Merely by ways of example, the determination unit 424 may determine mean values of x coordinates and y coordinates of the plurality of points, and designate the mean value of the x coordinates of the plurality of points as the x coordinate of the center point of the intervertebral disc and the mean value of the y coordinates of the plurality of points as the y coordinate of the center point of the intervertebral disc. In some embodiments, the determination unit 424 may determine directions of the plurality of points on an intervertebral disc center, and determine a direction of the intervertebral disc based on the directions of the plurality of points and the point-direction-mean value set. Merely by ways of example, the determination unit 424 may determine a mean value of directions of the plurality of points, and designate the mean value as the direction of the intervertebral disc. The determination of the position and the orientation of the at least one intervertebral disc may be disclosed elsewhere in the present disclosure, for example, FIG. 9, and the descriptions thereof.

Figure 7:
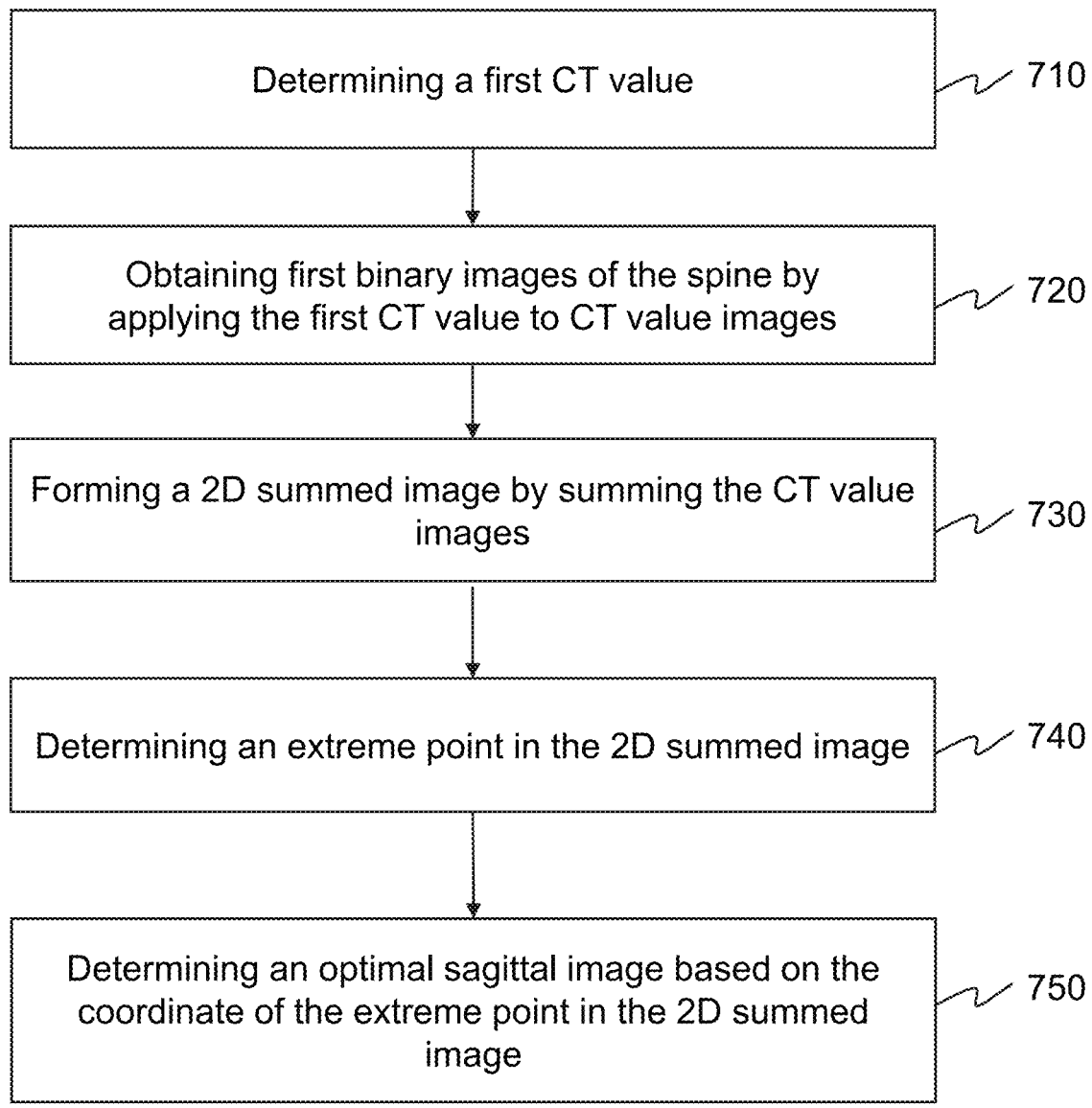
FIG. 7 is a flow chart illustrating an exemplary process 700 for identifying an optimal sagittal image within the CT value images according to some embodiments of the present disclosure.

FIG. 7 is a flow chart illustrating an exemplary process 700 for identifying an optimal sagittal image within the CT value images according to some embodiments of the present disclosure. In some embodiments, the operations in 610 in the process 600 may be performed according to the process 700. In some embodiments, the process 700 may be executed by the processing module 420. For example, the process 700 may be implemented as a set of instructions stored in the storage device 130, and/or the storage module 430. The processing apparatus 120 and/or the CPU 220 may execute the set of instructions and may accordingly be directed to perform the process 700. In some embodiments, the operations below in the process 700 may be performed by the first processing unit 422.

In 710, a first CT value may be determined. In some embodiments, the first CT value may be determined by the first processing unit 422. The first CT value may be a threshold used to separate bones from soft tissues in CT value images generated by scanning a spine of a subject. In some embodiments, the first CT value may be identified by a user (e.g., a technician), according to default settings of the imaging system 100. In some embodiments, the first CT value may be determined according to actual requirements. For example, since a spine is a longest bone structure for human without concerning arms and legs, CT values of bones of the spine are generally larger than 150 Hounsfield unit (Hu), and CT values of soft tissues are generally smaller than 150 Hu, the imaging system 100 may determine the first CT value as 150 Hu to separate bones from soft tissues in a CT value image.

In 720, first binary images of the spine may be obtained by applying the first CT value to the CT value images. After the first CT value is identified, a thresholding operation may be performed on the CT value images. The thresholding operation refers to an image segmentation using a threshold (e.g., the first CT value). The imaging system 100 may compare a CT value of each pixel in the CT value images with the first CT value. If the CT value of the pixel in the CT value images is larger than or equal to the first CT value, the CT value of the pixel may be set to a first value (e.g., 1). If the CT value of the pixel in the CT value images is smaller than the first CT value, the CT value of the pixel may be set to a second value (e.g., 0). It should be noted that each of the CT value images of the spine may be a binary image.

Figure 11A:
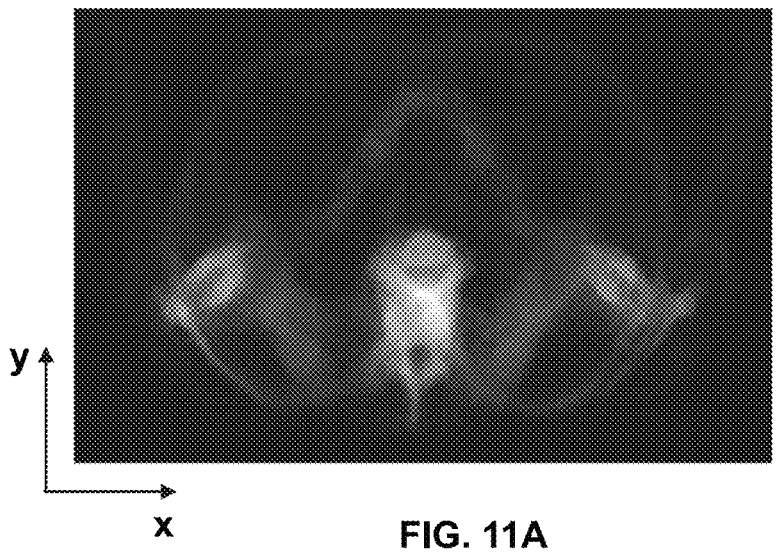
FIG. 11A illustrates an exemplary 2D summed image according to some embodiments of the present disclosure.

In 730, a 2D summed image may be formed by summing the first binary images. The operation that summing the first binary images corresponding to the plurality of original CT images may also be referred to as "pixel addition". In some embodiments, the first binary images may have a same size and a same number of pixels. Each pixel may correspond to a value (e.g., the first value or the second value). The imaging system 100 may determine a value of a pixel in the 2D summed image by summing values of corresponding pixels in the first binary images. For example, a value of a selected pixel Q(x, y) in the 2D summed image may be determined according to Equation (1):

$$Q(x,y)=P_1(x,y)+P_2(x,y)+\ldots+P_m(x,y)+\ldots+P_n(x,y)$$

where x and y denote a coordinate of a pixel in a 2D image, Q(x, y) denotes the value of the selected pixel in the 2D summed image, m denotes an integer between 2 and n, n denotes the number of the first binary images, and $P_1(x, y)$, $P_2(x, y)$, $P_m(x, y)$, and $P_n(x, y)$ denote values of corresponding pixels in the first binary images. The 2D summed image may have a same size as each of the first binary images. Merely for illustration purposes, FIG. 11A illustrates an exemplary 2D summed image according to some embodiments of the present disclosure.

Figure 11B:
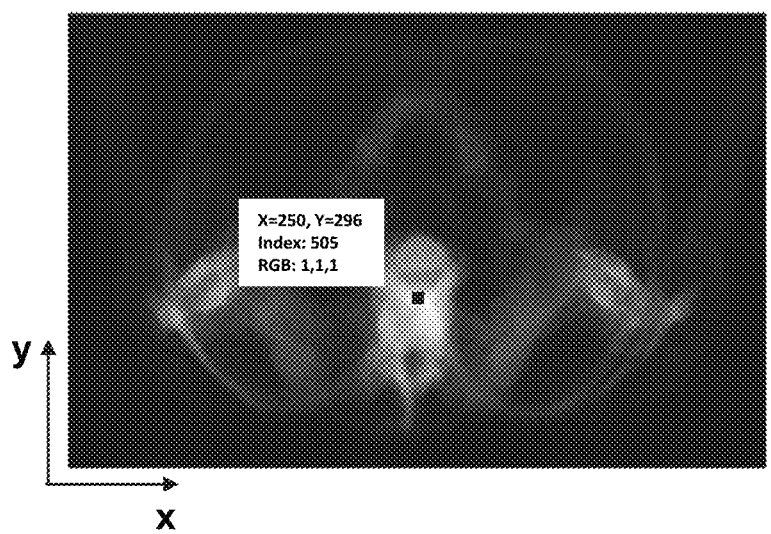
FIG. 11B illustrates an exemplary extreme point in an 2D summed image according to some embodiments of the present disclosure.

In 740, an extreme point in the 2D summed image may be determined. Each pixel in the 2D summed image may have a certain value. In some embodiments, the imaging system 100 may identify a pixel from the pixels of the 2D summed image which has a maximum value. The identified pixel may be designated as the extreme point in the 2D summed image. Merely for illustration purposes, FIG. 11B illustrates an exemplary extreme point in an 2D summed image according to some embodiments of the present disclosure. In some embodiments, the 2D summed image as illustrated in FIG. 11B may be the same as the 2D summed image in FIG. 11A. In some embodiments, the location of the extreme point may be represented by a coordinate (e.g., in forms of x and y). In some embodiments, an index and/or an RGB value of the extreme point may also be determined. For example, the imaging system 100 may encode each pixel in the 2D summed image with an index, and the index of the extreme point may be determined after the first processing unit 422 determines the extreme point.

Figure 11C:
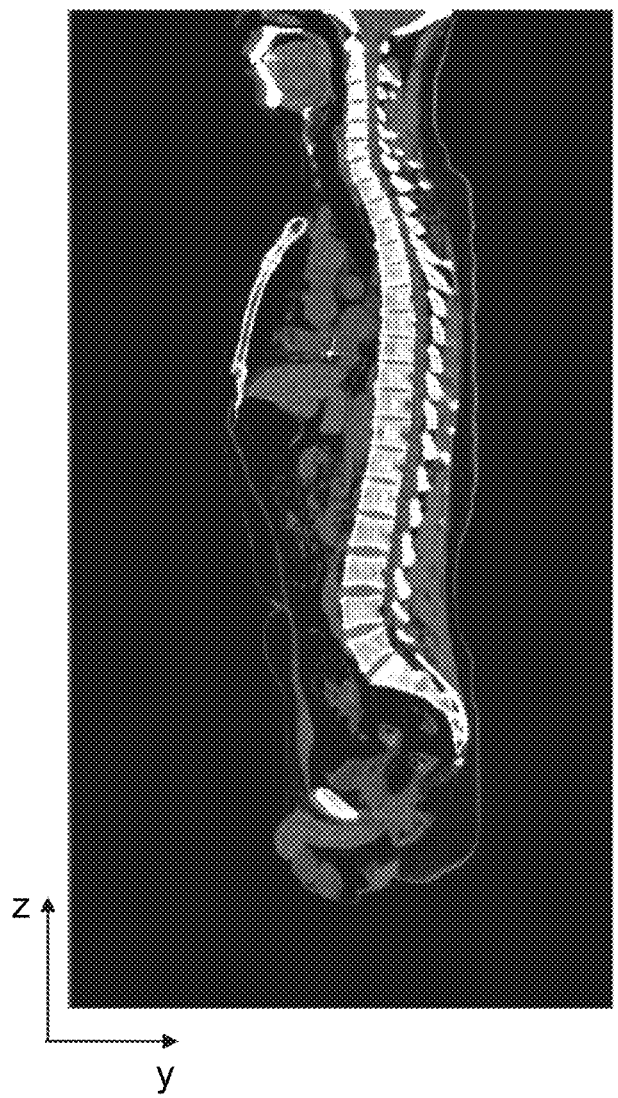
FIG. 11C illustrates an exemplary optimal sagittal image according to some embodiments of the present disclosure.

In 750, an optimal sagittal image may be determined based on the coordinate of the extreme point in the 2D summed image. In some embodiments, the 2D summed image may be in the x-y plane. In some embodiments, the imaging system 100 may determine an image of the spine in the y-z plane including the extreme point based on the CT value images. For example, the imaging system 100 may identify the extreme point in the CT value images of the spine of the subject based on the coordinates and/or index of the extreme point, and determine the image in the y-z plane including the extreme point. Since the determined image is in the y-z plane and includes the extreme point, the first processing unit 422 may designate the determined image as the optimal sagittal image. Merely for illustration purposes, FIG. 11C illustrates an exemplary optimal sagittal image according to some embodiments of the present disclosure.

Figure 8:
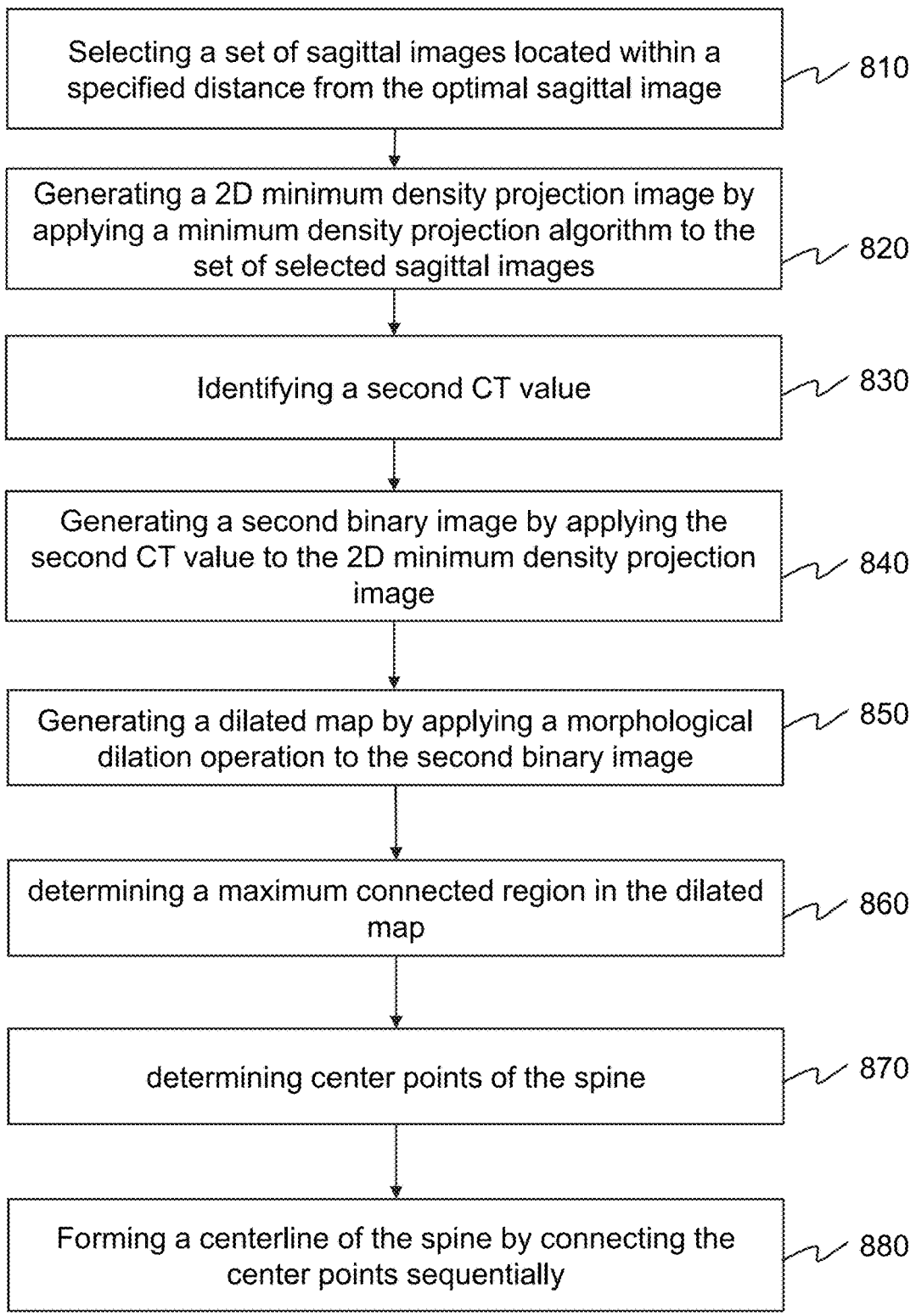
FIG. 8 is a flowchart illustrating an exemplary process 800 for identifying a centerline of the spine within the optimal sagittal slice according to some embodiments of the present disclosure.

FIG. 8 is a flowchart illustrating an exemplary process 800 for identifying a centerline of the spine within the optimal sagittal slice according to some embodiments of the present disclosure. In some embodiments, the operations in 620 of the process 600 may be performed according to the process 800. In some embodiments, the process 800 may be executed by the processing module 420. For example, the process 800 may be implemented as a set of instructions stored in the storage device 130, and/or the storage module 430. The processing apparatus 120 and/or the CPU 220 may execute the set of instructions and may accordingly be directed to perform the process 800. In some embodiments, the operations below in the process 800 may be performed by the second processing unit 423.

In 810, a set of sagittal images located within a specified distance from the optimal sagittal image may be selected. The set of sagittal images may be parallel to the optimal sagittal image determined in 750 of the process 700. The specified distance may be determined by a user, according to default settings of the imaging system 100. For example, the distance may be an integral multiple of the thickness of a 2D slice represented by a sagittal image. In some embodiments, the specified distance may be determined according to a structure of the spine of the subject. To be specific, the specified distance may be determined according to a radius of a spinal aperture of an adult. For example, specified distance may be set to 4 millimeters so as to separate a cristae from the spine and remove a portion of cristae out of the image obtained in the following operations.

Figure 12A:
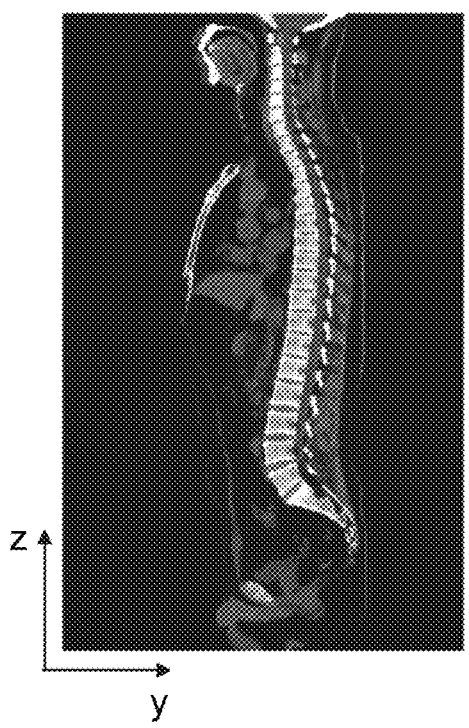
FIG. 12A illustrates an exemplary 2D minimum density projection image according to some embodiments of the present disclosure.

In 820, a 2D minimum density projection image may be generated by applying a minimum density projection (MinIP) algorithm to the set of selected sagittal images. In some embodiments, the set of selected sagittal images may have a same size and a same number of pixels. Each pixel of each selected sagittal images may correspond to a value (e.g., a CT value corresponding to the pixel). The second processing unit 423 may determine a value of a selected pixel in the 2D minimum density projection image by identifying a minimum value from values of corresponding pixels in the set of selected sagittal images. For example, a value of a selected pixel V(x, y) in the 2D minimum density projection image may be determined according to Equation (2):

$$V(x,y)=\text{Min}\{W_1(x,y), W_2(x,y), \ldots, W_m(x,y), \ldots, W_n(x,y)\}$$

where x and y denote a coordinate of a pixel in a 2D image, V(x, y) denotes the value of the selected pixel in the 2D minimum density projection image, m denotes an integer between 2 and n, n denotes the number of the set of selected sagittal images, and $W_1(x, y)$, $W_2(x, y)$, $W_m(x, y)$, and $W_n(x, y)$ denote values of corresponding pixels in the set of selected sagittal images. The 2D minimum density projection image may have a same size as each selected sagittal image. Merely for illustration purposes, FIG. 12A illustrates an exemplary 2D minimum density projection image according to some embodiments of the present disclosure.

In 830, a second CT value may be identified. The second CT value may also be used to separate bones from soft tissues in the 2D minimum density projection image including the spine of the subject. In some embodiments, the second CT value may be identified by a user (e.g., a technician), according to default settings of the imaging system 100. In some embodiments, the second CT value may be determined according to actual requirements. For example, the imaging system 100 may determine the second CT value threshold to be 100 Hu.

Figure 12B:
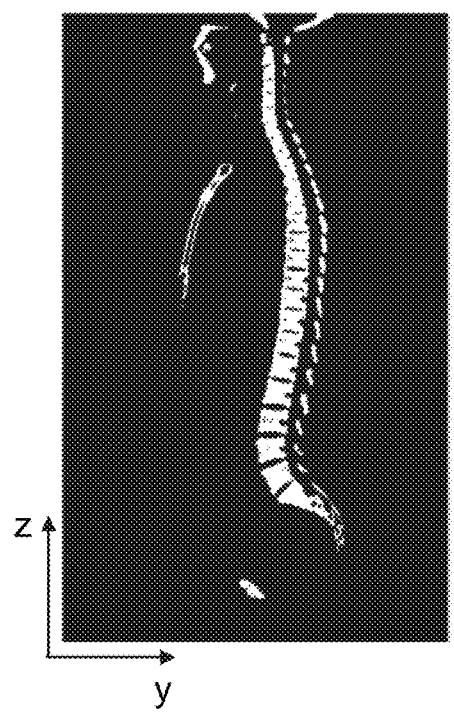
FIG. 12B illustrates an exemplary second binary image according to some embodiments of the present disclosure.

In 840, a second binary image may be generated by applying the second CT value to the 2D minimum density projection image. After the second CT value is determined, a thresholding operation may be performed on the 2D minimum density projection image. The thresholding operation may refer to image segmentation using a threshold (e.g., the second CT value). The imaging system 100 may generate the second binary image by comparing the value of each pixel in the 2D minimum density projection image with the second CT value. If the value of the pixel in the 2D minimum density projection image is larger than or equal to the second CT value, the value of the pixel in the second binary image may be set to a third value (e.g., 1). In some embodiments, the third value may be equal to the first value. If the value of the pixel in the 2D minimum density projection image is smaller than the second CT value, the value of the pixel in the second binary image may be set to a fourth value (e.g., 0). In some embodiments, the fourth value may be equal to the second value. Merely for illustration purposes, FIG. 12B illustrates an exemplary second binary image according to some embodiments of the present disclosure.

In 850, a dilated map may be generated by applying a morphological dilation operation to the second binary image. The morphological dilation operation may connect bones in the second binary image into a connected region. The morphological dilation operation may be used to merge one or more discontinuous regions into one region. For example, since adjacent bones of the spine may be separated by intervertebral discs, the separated bones may be connected using the morphological dilation operation. In some embodiments, the imaging system 100 may determine a vertical structon before the morphological dilation operation is performed. The vertical structon may be determined by a user, according to default settings of the imaging system 100. In some embodiments, the vertical structon may be an empirical value. For example, the vertical structon may be $[1, 1, 1, \ldots]^T$. In some embodiments, the vertical structon may be determined according to thicknesses of intervertebral discs in the spine of the subject. For example, the size of the vertical structon may be set to 10/p, where p denotes the thickness of a cross-sectional image, since the thicknesses of intervertebral discs of a human are smaller than 10 millimeters.

Figure 12C:
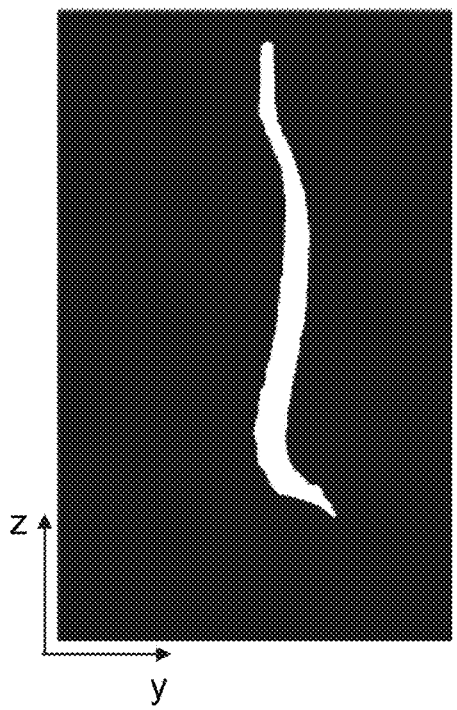
FIG. 12C illustrates an exemplary maximum connected region in the dilated map according to some embodiments of the present disclosure.

In 860, a maximum connected region in the dilated map may be determined. In some embodiments, there may be more than one connected region in the dilated map. Each of the more than one connected region may has a certain size. The imaging system 100 may determining a connected region R with a maximum size in the dilated map as the maximum connected region. The maximum connected region may be an outline of the spine, which is used for determining a center line of the spine, after structures such as the cristae of the spine are removed. Merely for illustration purposes, an exemplary maximum connected region in the dilated map may be illustrated in FIG. 12C.

In some embodiments, there may be holes between or within connected regions in the dilated map, which may decrease an accuracy of the calculation of the maximum connected region. During the process for determining the maximum connected region, a morphological closing operation may be performed so as to remove or eliminate the holes between or within connected regions as well as process boundaries of the spine in the dilated map. In some embodiments, the imaging system 100 may perform the morphological closing operation using a structon. The structon may be determined by a user, according to default settings of the imaging system. In some embodiments, the structon may be determined according to actual requirements. For example, a circular structon with a radius larger than the thickness of an intervertebral disc may be selected. Merely for illustration purposes, the circular structon may have a radius of 8/p, where p denotes the thickness of a cross-sectional image. The circular structon may move along a preliminary centerline of the spine at a preset step length (e.g., 30 millimeter) and perform a mean-value smoothing on the preliminary centerline.

As used herein, the preliminary centerline refers to a calculated centerline of the spine, rather than an actual centerline of the spine (also referred as "spine centerline"). The preliminary centerline may be composed of a plurality of preliminary points. The plurality of preliminary points may be determined according to the outline of the spine represented by the maximum connected region. For example, the second processing unit 423 may determine a plurality of horizontal straight line, each of which intersects with the outline of the spine represented by the maximum connected region at two points, and a midpoint of the two points may be designated as a preliminary point. As another example, the second processing unit 423 may determine a plurality of vertical straight line, each of which intersects with the outline of the spine represented by the maximum connected region at two points, and a midpoint of the two points may be designated as a preliminary point.

In 870, center points of the spine may be identified. In some embodiments, a set of center points may be determined after the second processing unit 423 performs the mean-value smoothing on the preliminary centerline with the circular structon. The set of center points may be on the spine centerline, and the second processing unit 423 may determine the spine centerline by connecting the set of center points. The set of center points may be represented by Equation (3):

$$P=\{\ldots, <x_i, y_i>, \ldots\}, \quad (3)$$

where P denotes the set of center points, $x_i$ denotes the x coordinate of an i-th point in the set of center points, and $y_i$ denotes the y coordinate of an i-th point in the set of center points.

Figure 12D:
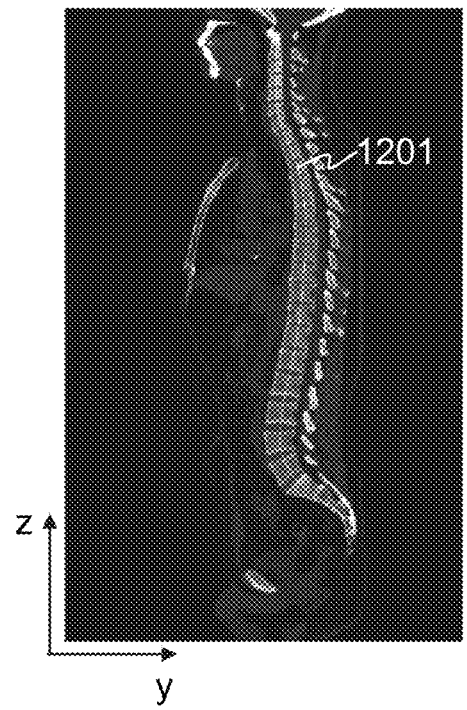
FIG. 12D illustrates an exemplary spine centerline according to some embodiments of the present disclosure.

In 880, the spine centerline may be formed by connecting the set center points sequentially. In some embodiments, two sequential center points may be connected using a straight line segment. In some embodiments, two sequential center points may be connected using a curved line segment. Merely for illustration purposes, an exemplary spine centerline may be illustrated in FIG. 12D. As shown in FIG. 12D, the curve 1201 may be the centerline of the spine of the subject.

Figure 9:
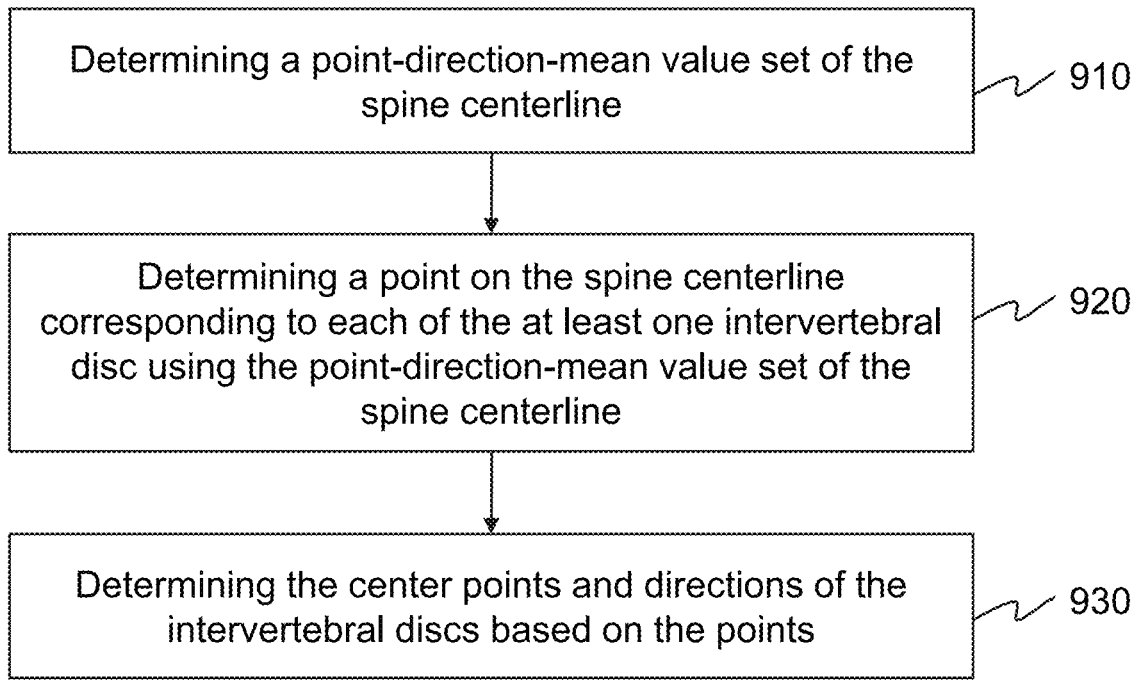
FIG. 9 is a flowchart illustrating an exemplary process 900 for identifying a center and an orientation of at least one intervertebral disc along the spine centerline according to some embodiments of the present disclosure.

FIG. 9 is a flowchart illustrating an exemplary process 900 for identifying a center and an orientation of at least one intervertebral disc along the spine centerline according to some embodiments of the present disclosure. In some embodiments, the operations in 630 in the process 600 may be performed according to the process 900. In some embodiments, the process 900 may be executed by the processing module 420. For example, the process 900 may be implemented as a set of instructions stored in the storage device 130, and/or the storage module 430. The processing apparatus 120 and/or the CPU 220 may execute the set of instructions and may accordingly be directed to perform the process 900. In some embodiments, the operations below in the process 900 may be performed by the first processing unit 422.

In 910, a point-direction-mean value set of the spine centerline may be determined. The point-direction-mean value set may include a plurality of elements. Each element may represent a point on the spine centerline, which includes a mean value associated with the point, and a direction associated with the point.

The imaging system 100 may determine each element of the point-direction-mean value set based on the dilated map including the spine centerline (e.g., the dilated map as illustrated in FIG. 12D). In some embodiments, for a point (i.e., a center point) on the spine centerline, a straight line being in a certain direction (e.g., perpendicular to the spine centerline in the y-z plane) that passes through the point may be determined. The straight line may intersect with the outline of the spine represented by the maximum connected region at two points. The imaging system 100 may select pixels along the straight line between the two points, and obtain values of the pixels on the straight line. In some embodiments, a mean value associated with the straight line may be determined by determining an average value of the obtained values of the pixels. In some embodiments, a set of straight lines may be determined by rotating the straight line around the point at a preset step each time. For example, the imaging system 100 may rotate the straight line around the point at a step of 1 degrees each time, and determine the set of straight lines after the straight line is rotated over 30 degrees. Similarly, mean values associated with the straight lines may be determined. Then the imaging system 100 may identify a minimum mean value from the mean values associated with the straight lines in different directions that pass through the point on the spine centerline. In some embodiments, the minimum mean value may be designated as a mean value associated with the point. In some embodiments, the direction of the straight line corresponding to the minimum mean value may be designated as the direction associated with the point. The point, the mean value associated with the point, and the direction associated with the point may constitute an element of the point-direction-mean value set related to the point. In some embodiments, the imaging system may determine indexes of points on the spine centerline, and represent each point with an index.

In some embodiments, the imaging system 100 may identify the plurality of points on the spine centerline, and determine the point-direction-mean value set by determining each element of the point-direction-mean value set related to a point of the plurality of points on the spine centerline. Merely for illustration purposes, the point-direction-mean value set of the spine centerline may be determined by performing the following operations. A point $p_i=(x_i,y_i)$ may be selected from the spine centerline. A direction vector of the point $p_i$ and a normal vector of the point $p_i$ may be determined, for example, according to the Equations (4) through (5):

$$d_i = \text{Norm}(p_{i+1}-p_{i-1}) = \text{Norm}(x_{i+1}-x_{i-1}, y_{i+1}-y_{i-1}), \quad (4)$$

$$d_i^\perp = \text{Norm}(y_{i+1}-y_{i-1}, x_{i-1}-x_{i+1}), \quad (5)$$

where Norm denotes a normalization operation, $d_i$ denotes the direction vector of the point $p_i$, and $d_i^\perp$ denotes the normal vector of the point $p_i$, and $d_i$ is perpendicular to $d_i^\perp$ (i.e., $d_i \cdot d_i^\perp = 0$).

The direction of the normal vector $d_i^\perp$ may be designated as an initial direction, which is represented by an initial vector $d_{cur}$ (i.e., $d_{cur}=d_i^\perp$). A positive direction and a negative direction of the initial vector $d_{cur}$ may form a straight line, which intersects the spine region R at two points. Pixels between the two points may be obtained, and a mean value of the pixels may be represented by $M_{cur}$. Then the initial vector $d_{cur}$ may be rotated around the point $p_i$ at an incremental change of 1 degree. A current direction after rotation may be determined according to Equation (6) and (7):

$$M_{rot} = \begin{bmatrix} \cos\theta & -\sin\theta \\ \sin\theta & \cos\theta \end{bmatrix}, \quad (6)$$

$$d'_{cur} = M_{rot} \cdot d_i^\perp, \quad (7)$$

where $M_{rot}$ denotes a rotation matrix, $d_{cur}'$ denotes a vector representing the current direction after rotation. After the initial vector is rotated over a range of (−15°, +15°) relative to the initial vector $d_{cur}$, the imaging system 100 may determine multiple mean values (e.g., 31 mean values) associated with different directions. The imaging system 100 may identify a minimum mean value $m_i$ from the multiple mean values. In some embodiments, the minimum mean value $m_i$ may be designated as a the mean value associated with the point $p_i$. In some embodiments, the direction $d_i'$ corresponding to the minimum mean value $m_i$ may be designated as the direction associated with the point.

The imaging system 100 may identify the plurality of center points on the spine centerline, and determine the point-direction-mean value set S by determining each element of the point-direction-mean value set related to a point of the plurality of center points on the spine centerline. The point-direction-mean value set S may be represented according to Equation (8):

$$S=\{\ldots, <p_i, d_i', m_i>, \ldots\}, \quad (8)$$

where $<p_i, d_i', m_i>$ denotes an element in the point-direction-mean value set S.

Figure 13:
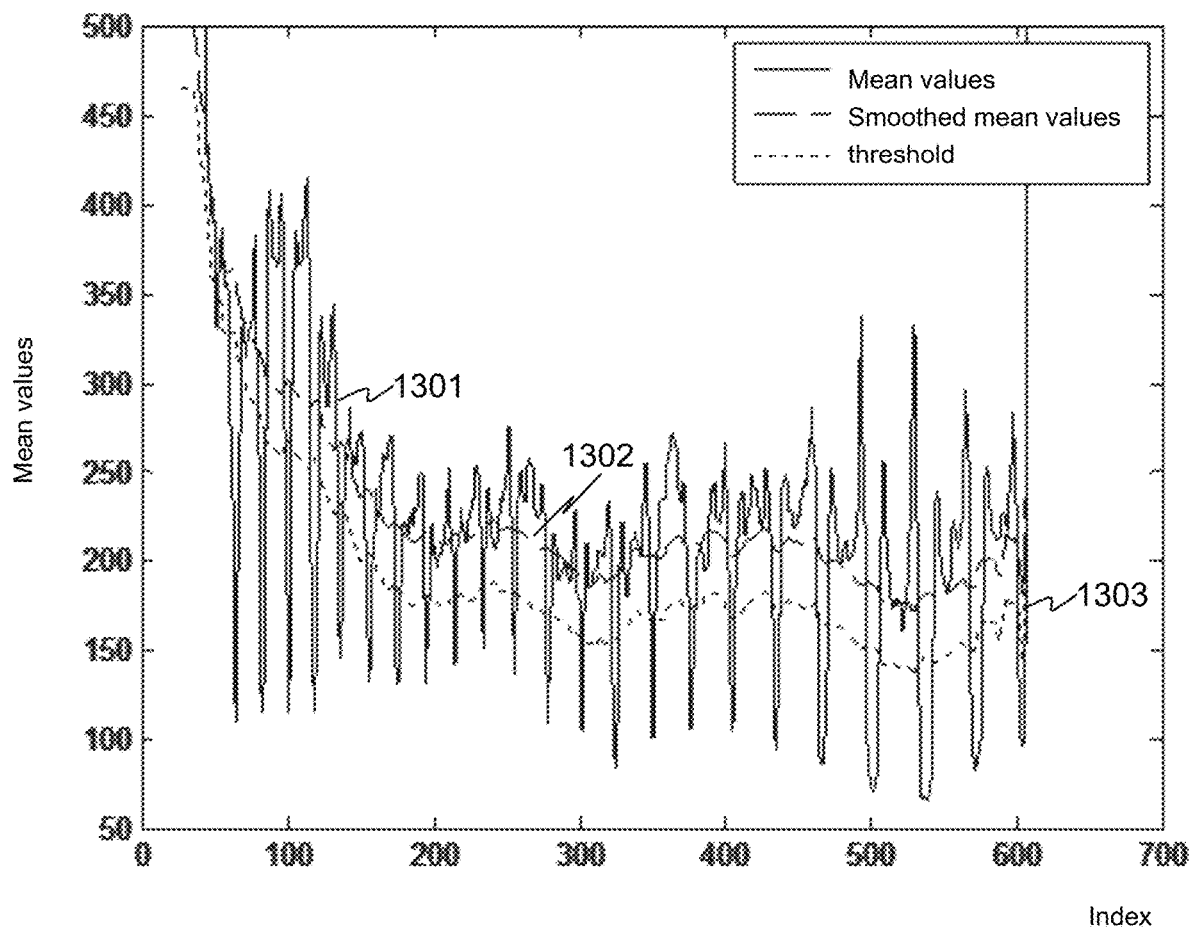
FIG. 13 illustrates an exemplary point-mean value curve according to some embodiments of the present disclosure.

In 920, a point on the spine centerline corresponding to each of the at least one intervertebral disc may be determined using the point-direction-mean value set of the spine centerline. In some embodiments, the determination unit 424 may determine, based on the point-direction-mean value set of the spine centerline, a point-mean value curve represented in a schematic diagram, for example, FIG. 13. As illustrated in FIG. 13, The horizontal axis of the schematic diagram represents indexes of points on the spine centerline, and the vertical axis of the schematic diagram represents mean values of the points. In some embodiments, the imaging system 100 may determine the position of the at least one intervertebral disc by processing the point-mean value curve. In some embodiments, a smoothed point-mean value curve 1302 (also referred to as "trend curve") may be determined by smoothing the point-mean value curve 1301 with a certain smoothing radius (e.g., 32 millimeters). Merely by ways of example, a one-dimension mean value smoothing may be used to smooth the point-mean value curve. The smoothed mean value of the point-mean value curve may be determined according to Equation (9):

$$m_i = \text{Avg}(m_{i-r}, m_{i-r+1}, \ldots, m_{i+r}), \quad (9)$$

where Avg denotes an averaging operation, and r denotes a smoothing radius.

In some embodiments, a threshold trend curve 1303 may be determined by shifting the trend curve 1302 downwards by a certain value (e.g., an empirical value of 35). Then the imaging system 100 may determine the position of the at least one intervertebral disc based on the threshold trend curve 1303. To be specific, each nadir of the point-mean value curve below the threshold trend curve 1303 may correspond to an intervertebral disc center. The intervertebral disc center in the thickness direction herein refers to a line segment crossing the center of the intervertebral disc in the thickness direction. The line segment may include a plurality of points on the intervertebral disc center.

Figure 14:
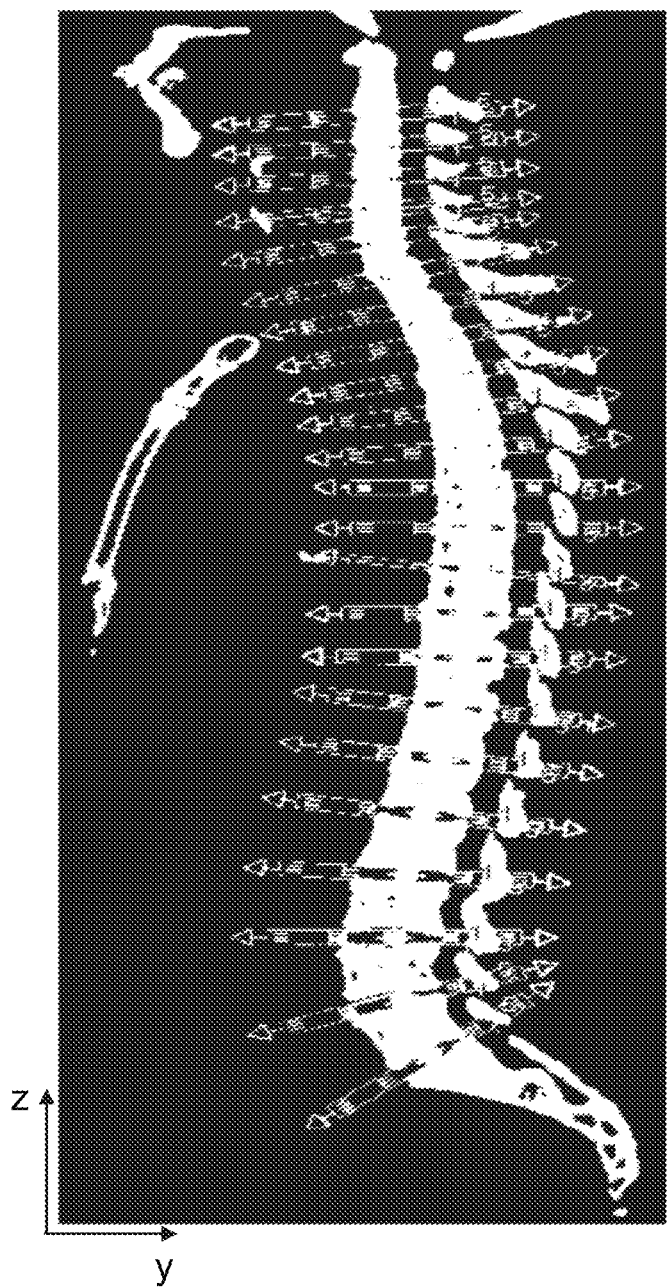
FIG. 14 illustrates exemplary center points and directions of intervertebral discs according to some embodiments of the present disclosure.

In 930, the center point and the direction of the at least one intervertebral disc may be determined based on the points. The direction of the at least one intervertebral disc refers to a direction perpendicular to the thickness direction of the at least one intervertebral disc. The center point of an intervertebral disc refers to a geometric center point of the intervertebral disc on the intervertebral disc center. Since the intervertebral disc center of each intervertebral disc is a line segment including a plurality of points on the intervertebral disc center, the plurality of points on each intervertebral disc center may be determined by checking the index corresponding to each nadir of the point-mean value curve. In some embodiments, the determination unit 424 may determine coordinates of the plurality of points on an intervertebral disc center, and determine a center point of the intervertebral disc based on the coordinates of the plurality of points and the point-direction-mean value set. Merely by ways of example, the determination unit 424 may determine mean values of x coordinates and y coordinates of the plurality of points, and designate the mean value of the x coordinates of the plurality of points as the x coordinate of the center point of the intervertebral disc and the mean value of the y coordinates of the plurality of points as the y coordinate of the center point of the intervertebral disc. In some embodiments, the determination unit 424 may determine directions of the plurality of points on an intervertebral disc center, and determine a direction of the intervertebral disc based on the directions of the plurality of points and the point-direction-mean value set. Merely by ways of example, the determination unit 424 may determine a mean value of directions of the plurality of points, and designate the mean value as the direction of the intervertebral disc. Merely for illustration purposes, exemplary center points and directions of intervertebral discs may be illustrated in FIG. 14. As shown in FIG. 14, the directions of the intervertebral discs in the spine of the subject may be represented with arrows pointing to different directions. Since the center point and direction of each intervertebral disc is determined, the plane on which the each intervertebral disc is determined and the imaging system 100 may reconstruct an image of at least one intervertebral disc based on CT data on the plane.

At least one intervertebral disc may be positioned by determining the center point and the direction of the at least one intervertebral disc according to the operations or algorithms set forth above. In some embodiments, multiple planar images of the at least one intervertebral disc may be reconstructed in a three-dimensional space, which is realized using a multiple planar reconstruction (MPR) for each intervertebral disc. Merely for illustration purposes, an MPR processing operation may be conducted according to a direction of an intervertebral disc selected by a user, and an MPR processing result may be output to the user, for example, via a display of a terminal device (e.g., the terminal device 140). The MPR processing result may provide an optimal view of the intervertebral disc, and enable a better observation of the intervertebral disc.

In some embodiments, intervertebral discs of the spine may be marked and labelled according to their positions. In some embodiments, the intervertebral discs may be marked and labelled using coordinates of center points of the intervertebral discs. For example, L1 (a first lumbar vertebra) has a z coordinate of a in a left post system (LPS). L2 (a second lumbar vertebra) has a z coordinate of b in the LPS. Then an intervertebral disc L1-L2 (i.e., an intervertebral disc between the first lumbar vertebra and the second lumbar vertebra) may be positioned by determining a point with a z coordinate between a and b in a intervertebral disc center point set. The intervertebral disc center point set may include center points of intervertebral discs. In some embodiments, the intervertebral disc center point set may be determined by according to the operations above.

In some embodiments, the spine of the subject may be segmented into a plurality of portions, for example, cervical vertebra, thoracic vertebra, and lumbar vertebra after each intervertebral disc in the spine is labelled. The plurality of portions may be displayed to a user separately. Thus, a user may select a certain portion according to actual requirements. For example, if the user choose to view the cervical vertebra, an interface of a terminal device may display an image of the cervical vertebra. The image of the cervical vertebra may include one or more marked intervertebral discs.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on at least one machine each of which has at least one processor and at least one storage device, the method comprising:
   identifying an optimal sagittal image in which a centerline of a spine is located based on CT value images and a thresholding operation, wherein the optimal sagittal image being a 2D image;

identifying the centerline of the spine within the optimal sagittal image; and reconstructing an image of at least one intervertebral disc of the spine based on the identified centerline of the spine and an image reconstruction algorithm;

identifying a center point and a direction of the at least one intervertebral disc along the centerline of the spine, wherein the reconstructing an image of at least one intervertebral disc of the spine based on the identified centerline of the spine includes:

reconstructing the image of the at least one intervertebral disc of the spine based on the center point and the direction of the at least one intervertebral disc along the centerline of the spine.

2. The method of claim 1, further including:

acquiring a plurality of original computed tomography (CT) images of the spine of the subject; and generating the CT value images of the spine of the subject by processing the plurality of original CT images.

3. The method of claim 2, wherein generating the CT value images of the spine of the subject includes:

processing the plurality of original CT images of the spine by removing artifacts from the original CT images, the artifacts including a signal from a bed on which the subject is placed during the acquisition of the original CT images; and converting a gray scale value of each pixel of the plurality of original CT images into a CT value of the each pixel.

4. The method of claim 1, wherein identifying the optimal sagittal image in which the centerline of the spine is located comprises:

obtaining a first value;

determining first binary images of the spine by applying the first value to the CT value images, the first binary images of the spine being a plurality of two-dimensional (2D) coronal slices;

forming a 2D summed image by summing the plurality of 2D coronal slices in the first binary images;

determining an extreme pixel in the 2D summed coronal image; and determining the optimal sagittal image based on the extreme pixel in the 2D summed image.

5. The method of claim 1, wherein identifying the centerline of the spine within the optimal sagittal image includes:

selecting a set of sagittal images located within a specified distance from the optimal sagittal image;

generating a 2D minimum density projection image by applying a minimum density projection algorithm to the set of selected sagittal images;

obtaining a second value;

generating a second binary image by applying the second value to the 2D minimum density projection image;

generating a dilated map by applying a morphological dilation operation to the second binary image that connect bones in the second binary image into a connected region;

determining a maximum connected region in the dilated map;

identifying center points of the spine; and connecting the center points sequentially to form the centerline of the spine.

6. The method of claim 1, wherein identifying the center point and the direction of the at least one intervertebral disc along the centerline of the spine includes:

determining a point-direction-mean value set of the centerline of the spine, the point-direction-mean value set including a mean value and a direction vector associated with each point on the centerline; and determining the center point and the direction of the at least one intervertebral disc using the point-direction-mean value set.

7. The method of claim 6, wherein determining the point-direction-mean value set of the spine centerline comprises:

for each point on the centerline, identifying a normal vector perpendicular to the centerline at the point;

identifying a set of direction vectors having directions within a specified range and at a specified incremental difference, the specified range encompassing the normal vector;

for each direction vector in the set of direction vectors, selecting a set of pixels along the direction vector and within the boundary of the spine; and determining a mean value associated with the direction vector as the mean value of the direction;

determining a minimum mean value among the mean values associated with the set of direction vectors;

designating the minimum mean value as the mean value associated with the each point on the centerline;

identifying a direction along which the minimum mean values associated with the each point on the centerline is identified; and designating the identified direction as the direction associated with the each point on the centerline.

8. The method of claim 7, wherein determining the center point and the direction of the at least one intervertebral disc comprises:

generating a point-mean value curve;

smoothing the curve with a predetermined smoothing radius;

shifting the curve down by a value;

identifying the center point of the at least one intervertebral disc based on nadirs of the smoothed curve; and determining the direction of the at least one intervertebral disc based on the point-direction-mean value set.

9. The method of claim 1, further including:

positioning an intervertebral disc by determining the center point and the direction of the intervertebral disc; and marking and labeling the intervertebral disc according to the position of the of the intervertebral disc.

10. A system, comprising:

at least one storage device storing a set of instructions; and at least one processor configured to communicate with the at least one storage device, wherein when executing the set of instructions, the at least one processor is directed to perform operations including:

identifying an optimal sagittal image in which a centerline of a spine is located based on CT value images and a thresholding operation, wherein the optimal sagittal image being a 2D image;

identifying the centerline of the spine within the optimal sagittal image; and reconstructing an image of at least one intervertebral disc of the spine based on the identified centerline of the spine and an image reconstruction algorithm;

identifying a center point and a direction of the at least one intervertebral disc along the centerline of the spine, wherein the reconstructing an image of at least one intervertebral disc of the spine based on the identified centerline of the spine includes:

reconstructing the image of the at least one intervertebral disc of the spine based on the center point and the direction of the at least one intervertebral disc along the centerline of the spine.

11. The system of claim 10, the operations further including:

acquiring a plurality of original computed tomography (CT) images of the spine of the subject; and generating the CT value images of the spine of the subject by processing the plurality of original CT images.

12. The system of claim 11, wherein generating the CT value images of the spine of the subject includes:

processing the plurality of original CT images of the spine by removing artifacts from the original CT images, the artifacts including a signal from a bed on which the subject is placed during the acquisition of the original CT images; and converting a gray scale value of each pixel of the plurality of original CT images into a CT value of the each pixel.

13. The system of claim 10, wherein identifying the optimal sagittal image in which the centerline of the spine is located comprises:

obtaining a first value;

determining first binary images of the spine by applying the first value to the CT value images, the first binary images of the spine being a plurality of two-dimensional (2D) coronal slices;

forming a 2D summed image by summing the plurality of 2D coronal slices in the first binary images;

determining an extreme pixel in the 2D summed coronal image; and determining the optimal sagittal image based on the extreme pixel in the 2D summed image.

14. The system of claim 10, wherein identifying the centerline of the spine within the optimal sagittal image includes:

selecting a set of sagittal images located within a specified distance from the optimal sagittal image;

generating a 2D minimum density projection image by applying a minimum density projection algorithm to the set of selected sagittal images;

obtaining a second value;

generating a second binary image by applying the second value to the 2D minimum density projection image;

generating a dilated map by applying a morphological dilation operation to the second binary image that connect bones in the second binary image into a connected region;

determining a maximum connected region in the dilated map;

identifying center points of the spine; and connecting the center points sequentially to form the centerline of the spine.

15. The system of claim 10, wherein identifying the center point and the direction of the at least one intervertebral disc along the centerline of the spine includes:

determining a point-direction-mean value set of the centerline of the spine, the point-direction-mean value set including a mean value and a direction vector associated with each point on the centerline; and determining the center point and the direction of the at least one intervertebral disc using the point-direction-mean value set.

16. The system of claim 15, wherein determining the point-direction-mean value set of the spine centerline comprises:

for each point on the centerline, identifying a normal vector perpendicular to the centerline at the point;

identifying a set of direction vectors having directions within a specified range and at a specified incremental difference, the specified range encompassing the normal vector;

for each direction vector in the set of direction vectors, selecting a set of pixels along the direction vector and within the boundary of the spine; and determining a mean value associated with the direction vector as the mean value of the direction;

determining a minimum mean value among the mean values associated with the set of direction vectors;

designating the minimum mean value as the mean value associated with the each point on the centerline;

identifying a direction along which the minimum mean values associated with the each point on the centerline is identified; and designating the identified direction as the direction associated with the each point on the centerline.

17. The system of claim 10, the operations further including:

positioning an intervertebral disc by determining the center point and the direction of the intervertebral disc; and marking and labeling the intervertebral disc according to the position of the of the intervertebral disc.

18. A non-transitory computer readable medium, comprising at least one set of instructions, wherein when executed by at least one processor of a computing device, the at least one set of instructions causes the computing device to perform a method, the method comprising:

identifying an optimal sagittal image in which a centerline of a spine is located based on CT value images and a thresholding operation, wherein the optimal sagittal image being a 2D image;

identifying the centerline of the spine within the optimal sagittal image; and reconstructing an image of at least one intervertebral disc of the spine based on the identified centerline of the spine and an image reconstruction algorithm;

identifying a center point and a direction of the at least one intervertebral disc along the centerline of the spine, wherein the reconstructing an image of at least one intervertebral disc of the spine based on the identified centerline of the spine includes:

reconstructing the image of the at least one intervertebral disc of the spine based on the center point and the direction of the at least one intervertebral disc along the centerline of the spine.

* * * * *